(12) United States Patent
Metzner et al.

(10) Patent No.: US 7,939,632 B2
(45) Date of Patent: May 10, 2011

(54) PROTEOLYTICALLY CLEAVABLE FUSION PROTEINS WITH HIGH MOLAR SPECIFIC ACTIVITY

(75) Inventors: Hubert Metzner, Marburg (DE); Thomas Weimer, Gladenbach (DE); Stefan Schulte, Marburg (DE)

(73) Assignee: CSL Behring GmbH, Marburg (DE)

( * ) Notice: Subject to any disclaimer, the term of this patent is extended or adjusted under 35 U.S.C. 154(b) by 463 days.

(21) Appl. No.: 12/000,739

(22) Filed: Dec. 17, 2007

(65) Prior Publication Data

US 2008/0260755 A1    Oct. 23, 2008

Related U.S. Application Data

(63) Continuation-in-part of application No. 11/812,016, filed on Jun. 14, 2007.

(60) Provisional application No. 60/819,620, filed on Jul. 11, 2006.

(30) Foreign Application Priority Data

Jun. 14, 2006   (EP) .................................... 06012262

(51) Int. Cl.
*A61K 38/36* (2006.01)
*A61K 38/38* (2006.01)
*A61K 38/48* (2006.01)
*C07K 14/76* (2006.01)

(52) U.S. Cl. ........ 530/362; 530/384; 514/15.2; 514/21.2

(58) Field of Classification Search .................... 530/363
See application file for complete search history.

(56) References Cited

U.S. PATENT DOCUMENTS

| 4,784,950 A | 11/1988 | Hagen et al. |
| 2005/0266533 A1 | 12/2005 | Ballance et al. |
| 2009/0298760 A1 | 12/2009 | Weimer et al. |

FOREIGN PATENT DOCUMENTS

| EP | 0 770 625 B1 | 5/1997 |
| EP | 1 444 986 A1 | 8/2004 |
| WO | WO 91/09125 | 6/1991 |
| WO | WO 96/01653 | 1/1996 |
| WO | WO 01/79271 A1 | 10/2001 |
| WO | WO 02/04598 A2 | 1/2002 |
| WO | WO 02/04598 A3 | 1/2002 |
| WO | WO 03/059935 A2 | 7/2003 |
| WO | WO 03/059935 A3 | 7/2003 |
| WO | WO 03/068934 A2 | 8/2003 |
| WO | WO 03/068934 A3 | 8/2003 |
| WO | WO 2004/021861 A2 | 3/2004 |
| WO | WO 2004/021861 A3 | 3/2004 |
| WO | WO 2004/081053 A1 | 9/2004 |
| WO | WO 2004/101739 A2 | 11/2004 |
| WO | WO 2004/101739 A3 | 11/2004 |
| WO | WO 2004/101740 A2 | 11/2004 |
| WO | WO 2004/101740 A3 | 11/2004 |
| WO | WO 2005/001025 A2 | 1/2005 |
| WO | WO 2005/001025 A3 | 1/2005 |
| WO | WO 2005/024044 A2 | 3/2005 |
| WO | WO 2005/024044 A3 | 3/2005 |
| WO | WO 2006/018204 A1 | 2/2006 |

OTHER PUBLICATIONS

European Search Report; dated Jan. 24, 2007 for App. No. 06012262.9-2403.
Chaudhury, C., et al., The Major Histocompatibility Complex-related Fc Receptor for IgG (FcRn) Binds Albumin and Prolongs Its Lifespan, *J. Exp. Med.*, 197(3): 315-322 (2003).
Discipio, R.G., et al., A Comparison of Human Prothrombin, Factor IX (Christmas Factor), Factor X (Stuart Factor), and Protein S, *Biochemistry*, 16(4): 698-706 (1977).
Erhardtsen, E., to General Haemostasis—The Evidence-Based Route, *Pathophysiol. Haemost. Thromb.*, 32(suppl 1): 47-52 (2002).
Ewenstein, B.M., et al., Pharmacokinetic Analysis of Plasma-Derived and Recombinant F IX Concentrates in Previously Treated Patients With Moderate or Severe Hemophilia B, *Transfusion*, 42: 190-197 (2002).
International Search Report; dated Aug. 22, 2006, for European Patent App. No. 06002359.5, filed Feb. 6, 2006.
Bettini R. et al., Book Review of "Handbook of Pharmaceutical Excipients," Third Edition, Arthur H. Kibbe (ed.), *Journal of Controlled Release*, vol. 71, pp. 352-53 (2001).
Colman R.W. et al. (eds.), Excerpts from "Homeostasis and Thrombosis: Basic Principles & Clinical Practice," 4$^{th}$ ed., Philadelphia, Lippincott Williams & Wilkins, 2001, pp. 34-35, 40-41, 103-104, 128-129, 159, 176 and 194.
Kurachi K. et al., "Isolation and Characterization of a cDNA Coding for Human Factor IX," *Proc. Natl. Acad. Sci. U.S.A. Biochemistry*, vol. 79, pp. 6461-64 (1982).
Lee G., Book Review of "Pharmaceutical Formulation Development of Peptides and Proteins" by Sven Frokjaer et al., *European Journal of Pharmaceutics and Biopharmaceutics*, vol. 50, p. 329 (2000).
Lindley C.M. et al., "Pharmacokinetics and Pharmacodynamics of Recombinant Factor Vila," *Clinical Pharmacology & Therapeutics*, vol. 55, No. 6, pp. 638-648 (1994).
Morrissey J.H. et al., "Quantitation of Activated Factor VII Levels in Plasma Using a Tissue Factor Mutant Selectively Deficient in Promoting Factor VII Activation," *The American Society of Hematology, Blood*, vol. 81, No. 3, pp. 734-44 (1993).

(Continued)

*Primary Examiner* — Suzanne M Noakes
*Assistant Examiner* — Marsha M Tsay
(74) *Attorney, Agent, or Firm* — Finnegan, Henderson, Farabow, Garrett & Dunner LLP

(57) ABSTRACT

The invention relates to therapeutic fusion proteins in which a coagulation factor is fused to a half-life enhancing polypeptide, and in which both are connected by a linker peptide that is proteolytically cleavable. The cleavage of such linkers liberates the coagulation factor from activity-compromising steric hindrance caused by the half-life enhancing polypeptide and thereby allows the generation of fusion proteins may show relatively high molar specific activity when tested in coagulation-related assays. Furthermore, the fact that the linker is cleavable can enhance the rates of inactivation and/or elimination after proteolytic cleavage of the peptide linker compared to the rates measured for corresponding therapeutic fusion proteins linked by the non-cleavable linker having the amino acid sequence GGGGGGV.

31 Claims, 3 Drawing Sheets

OTHER PUBLICATIONS

O'Reilly M.S. et al., "Antiangiogenic Activity of the Cleaved Conformation of the Serpin Antithrombin," *Science*, vol. 285, pp. 1926-28 (1999).

Prescott M. et al., "The Length of Polypeptide Linker Affects the Stability of Green Fluorescent Protein Fusion Proteins," *Analytical Biochemistry*, vol. 273, pp. 305-307 (1999).

Seligsohn U. et al., "Coupled Amidolytic Assay for Factor VII: Its Use with a Clotting Assay to Determine the Activity State of Factor VII," *The American Society of Hematology, Blood*, vol. 52, No. 5, pp. 978-988 (1978).

Shah A.M. et al., "Manipulation of the Membrane binding Site of Vitamin K-Dependent Proteins: Enhanced Biological Function of Human Factor VII," *Proc. Natl. Acad. Sci. U.S.A. Biochemistry*, vol. 95, pp. 4229-4234 (1998).

Syed S. et al., "Potent Antithrombin Activity and Delayed Clearance from the Circulation Characterize Recombinant Hirudin Genetically Fused to Albumin," *The American Society of Hematology, Blood*, vol. 89, No. 9, pp. 3243-3252 (1997).

Beattie, Wanda G. and Dugaiczyk, Achilles, "Structure and Evolution of Human α-fetoprotein Deduced From Partial Sequence of Cloned cDNA," *Gene*, 20: 415-422 (1982).

Cooke, Nancy E. and David, Vivek, E., "Serum Vitamin D-binding Protein is a Third Member of the Albumin and Alpha Fetoprotein Gene Family," *Journal of Clinical Investigation*, 76: 2420-2424 (1985).

Wesley, Louise C., et al., "PACE/Furin Can Process the Vitamin K-dependent Pro-factor IX Precursor within the Secretory Pathway," *The Journal of Biological Chemistry*, 268: 8458-8465 (1993).

Lichenstein, Henri, et al., "Afamin is a New Member of the Albumin, α-Fetoprotein, and Vitamin D-binding Protein Gene Family," *The Journal of Biological Chemistry*, 269: 18149-18154 (1994).

Mollerup, Inger, et al., "The Use of RP-HPLC for Measuring Activation and Cleavage of rFVlla During Purification," *Biotechnology and Bioengineering*, 48: 501-505 (1995).

White, Gilbert C., et al., "Recombinant Factor IX," *Thrombosis and Haemostasis*, 78: 261-265 (1997).

Aledort, L.M., "Comparative Thrombotic Event Incidence After Infusion of Recombinant Factor Vlla versus Factor VIII Inhibitor Bypass Activity," *Journal of Thrombosis and Haemostasis*, 2: 1700-1708 (2004).

Sheffield, William P., et al., "Effects of Genetic Fusion of Factor IX to Albumin on In Vivo Clearance in Mice and Rabbits," *British Journal of Haematology*, 126: 565-573 (2004).

International Search Report for application No. PCT/EP2007/005246, Sep. 28, 2007.

Bick R.L. et al., "Physiology of Hemostasis," *Clin. Lab. Med.*, 14(4):677-707 (1994).

Coleman R.W. et al., *Overview of Hemostasis*, in Hemostasis and Thrombosis $4^{th}$ Ed., Chapter 1 (Colman et al. eds., Lippincott Williams & Wilkins, 2001).

Greenberg D.L. et al., *Blood Coagulation Factors: Their Complementary DNAs, Genes, and Expression*, in Hemostasis and Thrombosis $4^{th}$ Ed., Chapter 3, (Colman et al. eds., Lippincott Williams & Wilkins, 2001).

US 7,939,632 B2

SEQUENCE LISTING

```
<160> NUMBER OF SEQ ID NOS: 114

<210> SEQ ID NO 1
<211> LENGTH: 585
<212> TYPE: PRT
<213> ORGANISM: Homo sapiens

<400> SEQUENCE: 1

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
```

```
                    260             265             270
Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 2
<211> LENGTH: 415
<212> TYPE: PRT
<213> ORGANISM: Homo sapiens

<400> SEQUENCE: 2

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
```

```
                50              55              60
Asp Ile Asn Ser Tyr Glu Cys Trp Cys Pro Phe Gly Phe Glu Gly Lys
 65                  70                  75                  80

Asn Cys Glu Leu Asp Val Thr Cys Asn Ile Lys Asn Gly Arg Cys Glu
                 85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 3
<211> LENGTH: 1386
<212> TYPE: DNA
<213> ORGANISM: Homo sapiens

<400> SEQUENCE: 3
atgcagcgcg tgaacatgat catggcagaa tcaccaggcc tcatcaccat ctgccttta      60 ggatatctac tcagtgctga atgtacagtt tttcttgatc atgaaaacgc caacaaaatt    120
```

| | | |
|---|---|---|
| ctgaatcggc caaagaggta taattcaggt aaattggaag agtttgttca agggaacctt | 180 | |
| gagagagaat gtatggaaga aaagtgtagt tttgaagaag cacgagaagt ttttgaaaac | 240 | |
| actgaaagaa caactgaatt ttggaagcag tatgttgatg gagatcagtg tgagtccaat | 300 | |
| ccatgtttaa atggcggcag ttgcaaggat gacattaatt cctatgaatg ttggtgtccc | 360 | |
| tttggatttg aaggaaagaa ctgtgaatta gatgtaacat gtaacattaa gaatggcaga | 420 | |
| tgcgagcagt tttgtaaaaa tagtgctgat aacaaggtgg tttgctcctg tactgaggga | 480 | |
| tatcgacttg cagaaaacca gaagtcctgt gaaccagcag tgccatttcc atgtggaaga | 540 | |
| gtttctgttt cacaaacttc taagctcacc cgtgctgaga ctgttttttcc tgatgtggac | 600 | |
| tatgtaaatt ctactgaagc tgaaaccatt ttggataaca tcactcaaag cacccaatca | 660 | |
| tttaatgact tcactcgggt tgttggtgga gaagatgcca aaccaggtca attcccttgg | 720 | |
| caggttgttt tgaatggtaa agttgatgca ttctgtggag gctctatcgt taatgaaaaa | 780 | |
| tggattgtaa ctgctgccca ctgtgttgaa actggtgtta aaattacagt tgtcgcaggt | 840 | |
| gaacataata ttgaggagac agaacataca gagcaaaagc gaaatgtgat tcgaattatt | 900 | |
| cctcaccaca actacaatgc agctattaat aagtacaacc atgacattgc ccttctggaa | 960 | |
| ctggacgaac ccttagtgct aaacagctac gttacaccta tttgcattgc tgacaaggaa | 1020 | |
| tacacgaaca tcttcctcaa atttggatct ggctatgtaa gtggctgggg aagagtcttc | 1080 | |
| cacaaaggga gatcagcttt agttcttcag taccttagag ttccacttgt tgaccgagcc | 1140 | |
| acatgtcttc gatctacaaa gttcaccatc tataacaaca tgttctgtgc tggcttccat | 1200 | |
| gaaggaggta gagattcatg tcaaggagat agtgggggac cccatgttac tgaagtggaa | 1260 | |
| gggaccagtt tcttaactgg aattattagc tggggtgaag agtgtgcaat gaaaggcaaa | 1320 | |
| tatggaatat ataccaaggt atcccggtat gtcaactgga ttaaggaaaa aacaaagctc | 1380 | |
| acttaa | 1386 | |

<210> SEQ ID NO 4
<211> LENGTH: 1830
<212> TYPE: DNA
<213> ORGANISM: Homo sapiens

<400> SEQUENCE: 4

| | | |
|---|---|---|
| atgaagtggg taacctttat ttcccttctt tttctctttta gctcggctta ttccaggggt | 60 | |
| gtgtttcgtc gagatgcaca caagagtgag gttgctcatc ggtttaaaga tttgggagaa | 120 | |
| gaaaatttca aagccttggt gttgattgcc tttgctcagt atcttcagca gtgtccattt | 180 | |
| gaagatcatg taaaattagt gaatgaagta actgaatttg caaaaacatg tgttgctgat | 240 | |
| gagtcagctg aaaattgtga caaatcactt catacccttt ttggagacaa attatgcaca | 300 | |
| gttgcaactc ttcgtgaaac ctatggtgaa atggctgact gctgtgcaaa acaagaacct | 360 | |
| gagagaaatg aatgcttctt gcaacacaaa gatgacaacc caaacctccc ccgattggtg | 420 | |
| agaccagagg ttgatgtgat gtgcactgct tttcatgaca atgaagagac attttttgaaa | 480 | |
| aaatacttat atgaaattgc cagaagacat ccttactttt atgccccgga actccttttc | 540 | |
| tttgctaaaa ggtataaagc tgcttttaca gaatgttgcc aagctgctga taaagctgcc | 600 | |
| tgcctgttgc caaagctcga tgaacttcgg gatgaaggga aggcttcgtc tgccaaacag | 660 | |
| agactcaagt gtgccagtct ccaaaaattt ggagaaagag ctttcaaagc atgggcagta | 720 | |
| gctcgcctga gccagagatt tcccaaagct gagtttgcag aagtttccaa gttagtgaca | 780 | |
| gatcttacca aagtccacac ggaatgctgc catggagatc tgcttgaatg tgctgatgac | 840 | |

-continued

```
agggcggacc ttgccaagta tatctgtgaa aatcaagatt cgatctccag taaactgaag    900
gaatgctgtg aaaaacctct gttggaaaaa tcccactgca ttgccgaagt ggaaaatgat    960
gagatgcctg ctgacttgcc ttcattagct gctgattttg ttgaaagtaa ggatgtttgc   1020
aaaaactatg ctgaggcaaa ggatgtcttc ctgggcatgt ttttgtatga atatgcaaga   1080
aggcatcctg attactctgt cgtgctgctg ctgagacttg ccaagacata tgaaaccact   1140
ctagagaagt gctgtgccgc tgcagatcct catgaatgct atgccaaagt gttcgatgaa   1200
tttaaacctc ttgtggaaga gcctcagaat ttaatcaaac aaaattgtga gcttttgag    1260 cagcttggag agtacaaatt ccagaatgcg ctattagttc gttacaccaa gaaagtaccc   1320
caagtgtcaa ctccaactct tgtagaggtc tcaagaaacc taggaaaagt gggcagcaaa   1380
tgttgtaaac atcctgaagc aaaaagaatg ccctgtgcag aagactatct atccgtggtc   1440
ctgaaccagt tatgtgtgtt gcatgagaaa acgccagtaa gtgacagagt caccaaatgc   1500
tgcacagaat ccttggtgaa caggcgacca tgcttttcag ctctggaagt cgatgaaaca   1560
tacgttccca agagtttaa tgctgaaaca ttcaccttcc atgcagatat atgcacactt    1620
tctgagaagg agagacaaat caagaaacaa actgcacttg ttgagctcgt gaaacacaag   1680
cccaaggcaa caaagagca actgaaagct gttatggatg atttcgcagc ttttgtagag    1740
aagtgctgca aggctgacga taaggagacc tgctttgccg aggagggtaa aaaacttgtt   1800
gctgcaagtc aagctgcctt aggcttataa                                    1830
```

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
ccactttcac aatctgctag c                                               21

<210> SEQ ID NO 6
<211> LENGTH: 23
<212> TYPE: DNA
<213> ORGANISM: Artificial Sequence
<220> FEATURE:
<223> OTHER INFORMATION: Synthetic

<400> SEQUENCE: 6
caattccaat gaattaacct tgg                                             23

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
atgcagcgcg tgaacatgat c                                               21

<210> SEQ ID NO 8
<211> LENGTH: 25
<212> TYPE: DNA
<213> ORGANISM: Artificial Sequence
<220> FEATURE:
<223> OTHER INFORMATION: Synthetic

<400> SEQUENCE: 8
tcattaagtg agctttgttt tttcc                                          25

<210> SEQ ID NO 9
<211> LENGTH: 21
<212> TYPE: DNA
<213> ORGANISM: Artificial Sequence
<220> FEATURE:
<223> OTHER INFORMATION: Synthetic

<400> SEQUENCE: 9
gattcgaatt cgcccttatg c                                              21

<210> SEQ ID NO 10
<211> LENGTH: 32
<212> TYPE: DNA
<213> ORGANISM: Artificial Sequence
<220> FEATURE:
<223> OTHER INFORMATION: Synthetic

<400> SEQUENCE: 10
cgctcgaggt gagctttgtt ttttccttaa tc                                  32

<210> SEQ ID NO 11
<211> LENGTH: 52
<212> TYPE: DNA
<213> ORGANISM: Artificial Sequence
<220> FEATURE:
<223> OTHER INFORMATION: Synthetic

<400> SEQUENCE: 11
ctcgagcggg ggatctggcg ggtctggagg ctctggaggg tcgggaggct ct            52

<210> SEQ ID NO 12
<211> LENGTH: 46
<212> TYPE: DNA
<213> ORGANISM: Artificial Sequence
<220> FEATURE:
<223> OTHER INFORMATION: Synthetic

<400> SEQUENCE: 12
ggatccagat cccccagagc ctccagagcc tcccgaccct ccagag                   46

<210> SEQ ID NO 13
<211> LENGTH: 56
<212> TYPE: DNA
<213> ORGANISM: Artificial Sequence
<220> FEATURE:
<223> OTHER INFORMATION: Synthetic

<400> SEQUENCE: 13
ctcgagcaat ggatctggcg ggtctggagg ctctggaggg tcgaatggct ctggag        56

<210> SEQ ID NO 14
<211> LENGTH: 64
<212> TYPE: DNA
<213> ORGANISM: Artificial Sequence
<220> FEATURE:
<223> OTHER INFORMATION: Synthetic

<400> SEQUENCE: 14
ggatccgttc cctccagacc cgccagatcc cccagagcct ccagagccat tcgaccctcc    60
agag                                                                 64

<210> SEQ ID NO 15
<211> LENGTH: 46
<212> TYPE: DNA

<213> ORGANISM: Artificial Sequence
<220> FEATURE:
<223> OTHER INFORMATION: Synthetic

<400> SEQUENCE: 15
cctcgagctc tgtgagccag acctccaagc tcaccagggc cgagac       46

<210> SEQ ID NO 16
<211> LENGTH: 44
<212> TYPE: DNA
<213> ORGANISM: Artificial Sequence
<220> FEATURE:
<223> OTHER INFORMATION: Synthetic

<400> SEQUENCE: 16
gggatccgtc cacatcaggg aagacagtct cggccctggt gagc       44

<210> SEQ ID NO 17
<211> LENGTH: 33
<212> TYPE: DNA
<213> ORGANISM: Artificial Sequence
<220> FEATURE:
<223> OTHER INFORMATION: Synthetic

<400> SEQUENCE: 17
ggaaaaaaca aagctcactt ctgtgagcca gac       33

<210> SEQ ID NO 18
<211> LENGTH: 33
<212> TYPE: DNA
<213> ORGANISM: Artificial Sequence
<220> FEATURE:
<223> OTHER INFORMATION: Synthetic

<400> SEQUENCE: 18
gtctggctca cagaagtgag ctttgttttt tcc       33

<210> SEQ ID NO 19
<211> LENGTH: 38
<212> TYPE: DNA
<213> ORGANISM: Artificial Sequence
<220> FEATURE:
<223> OTHER INFORMATION: Synthetic

<400> SEQUENCE: 19
cctcgagcag agcttcaatg acttcacccg ggtggtgg       38

<210> SEQ ID NO 20
<211> LENGTH: 41
<212> TYPE: DNA
<213> ORGANISM: Artificial Sequence
<220> FEATURE:
<223> OTHER INFORMATION: Synthetic

<400> SEQUENCE: 20
gggatccatc ctccccgccc accacccggg tgaagtcatt g       41

<210> SEQ ID NO 21
<211> LENGTH: 34
<212> TYPE: DNA
<213> ORGANISM: Artificial Sequence
<220> FEATURE:
<223> OTHER INFORMATION: Synthetic

<400> SEQUENCE: 21
ggaaaaaaca aagctcactc agagcttcaa tgac       34

<210> SEQ ID NO 22
<211> LENGTH: 34
<212> TYPE: DNA
<213> ORGANISM: Artificial Sequence
<220> FEATURE:
<223> OTHER INFORMATION: Synthetic

<400> SEQUENCE: 22
gtcattgaag ctctgagtga gctttgtttt ttcc                        34

<210> SEQ ID NO 23
<211> LENGTH: 31
<212> TYPE: DNA
<213> ORGANISM: Artificial Sequence
<220> FEATURE:
<223> OTHER INFORMATION: Synthetic

<400> SEQUENCE: 23
gtgggatccg atgcacacaa gagtgaggtt g                           31

<210> SEQ ID NO 24
<211> LENGTH: 35
<212> TYPE: DNA
<213> ORGANISM: Artificial Sequence
<220> FEATURE:
<223> OTHER INFORMATION: Synthetic

<400> SEQUENCE: 24
cacggatccc tataagccta aggcagcttg acttg                       35

<210> SEQ ID NO 25
<211> LENGTH: 18
<212> TYPE: DNA
<213> ORGANISM: Artificial Sequence
<220> FEATURE:
<223> OTHER INFORMATION: Synthetic

<400> SEQUENCE: 25
caaggagacg ggcgctcc                                          18

<210> SEQ ID NO 26
<211> LENGTH: 19
<212> TYPE: DNA
<213> ORGANISM: Artificial Sequence
<220> FEATURE:
<223> OTHER INFORMATION: Synthetic

<400> SEQUENCE: 26
gcccaaggag gggattggc                                         19

<210> SEQ ID NO 27
<211> LENGTH: 30
<212> TYPE: DNA
<213> ORGANISM: Artificial Sequence
<220> FEATURE:
<223> OTHER INFORMATION: Synthetic

<400> SEQUENCE: 27
gtggaattca tggagctgag gccctggttg                             30

<210> SEQ ID NO 28
<211> LENGTH: 38
<212> TYPE: DNA
<213> ORGANISM: Artificial Sequence
<220> FEATURE:
<223> OTHER INFORMATION: Synthetic -continued

```
<400> SEQUENCE: 28
cacgcggccg ctcactacag ccgttgcccc gcctccac                              38

<210> SEQ ID NO 29
<211> LENGTH: 704
<212> TYPE: PRT
<213> ORGANISM: Homo Sapiens

<400> SEQUENCE: 29
```

Met Glu Leu Arg Pro Trp Leu Leu Trp Val Val Ala Ala Thr Gly Thr
1               5                   10                  15

Leu Val Leu Leu Ala Ala Asp Ala Gln Gly Gln Lys Val Phe Thr Asn
            20                  25                  30

Thr Trp Ala Val Arg Ile Pro Gly Gly Pro Ala Val Ala Asn Ser Val
        35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
            100                 105                 110

Pro Thr Asp Pro Lys Phe Pro Gln Gln Trp Tyr Leu Ser Gly Val Thr
        115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asp Gly Ile Glu Lys Asn His
145                 150                 155                 160

Pro Asp Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
            180                 185                 190

Arg His Gly Thr Arg Cys Ala Gly Glu Val Ala Ala Val Ala Asn Asn
        195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
            260                 265                 270

Ala Phe Phe Arg Gly Val Ser Gln Gly Arg Gly Gly Leu Gly Ser Ile
        275                 280                 285

Phe Val Trp Ala Ser Gly Asn Gly Gly Arg Glu His Asp Ser Cys Asn
    290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
            340                 345                 350

Thr Thr Asp Leu Arg Gln Lys Cys Thr Glu Ser His Thr Gly Thr Ser
        355                 360                 365

Ala Ser Ala Pro Leu Ala Ala Gly Ile Ile Ala Leu Thr Leu Glu Ala
        370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
            405                 410                 415

Gly Arg Lys Val Ser His Ser Tyr Gly Tyr Gly Leu Leu Asp Ala Gly
        420                 425                 430

Ala Met Val Ala Leu Ala Gln Asn Trp Thr Thr Val Ala Pro Gln Arg
    435                 440                 445

Lys Cys Ile Ile Asp Ile Leu Thr Glu Pro Lys Asp Ile Gly Lys Arg
450                 455                 460

Leu Glu Val Arg Lys Thr Val Thr Ala Cys Leu Gly Glu Pro Asn His
465                 470                 475                 480

Ile Thr Arg Leu Glu His Ala Gln Ala Arg Leu Thr Leu Ser Tyr Asn
                485                 490                 495

Arg Arg Gly Asp Leu Ala Ile His Leu Val Ser Pro Met Gly Thr Arg
            500                 505                 510

Ser Thr Leu Leu Ala Ala Arg Pro His Asp Tyr Ser Ala Asp Gly Phe
        515                 520                 525

Asn Asp Trp Ala Phe Thr Thr Thr His Ser Trp Asp Glu Asp Pro Ser
530                 535                 540

Gly Glu Trp Val Leu Glu Ile Glu Asn Thr Ser Glu Ala Asn Asn Tyr
545                 550                 555                 560

Gly Thr Leu Thr Lys Phe Thr Leu Val Leu Tyr Gly Thr Ala Pro Glu
                565                 570                 575

Gly Leu Pro Val Pro Pro Glu Ser Ser Gly Cys Lys Thr Leu Thr Ser
            580                 585                 590

Ser Gln Ala Cys Val Val Cys Glu Glu Gly Phe Ser Leu His Gln Lys
        595                 600                 605

Ser Cys Val Gln His Cys Pro Pro Gly Phe Ala Pro Gln Val Leu Asp
610                 615                 620

Thr His Tyr Ser Thr Glu Asn Asp Val Glu Thr Ile Arg Ala Ser Val
625                 630                 635                 640

Cys Ala Pro Cys His Ala Ser Cys Ala Thr Cys Gln Gly Pro Ala Leu
                645                 650                 655

Thr Asp Cys Leu Ser Cys Pro Ser His Ala Ser Leu Asp Pro Val Glu
            660                 665                 670

Gln Thr Cys Ser Arg Gln Ser Gln Ser Ser Arg Glu Ser Pro Pro Gln
        675                 680                 685

Gln Gln Pro Pro Arg Leu Pro Pro Glu Val Glu Ala Gly Gln Arg Leu
    690                 695                 700

<210> SEQ ID NO 30
<211> LENGTH: 25
<212> TYPE: PRT
<213> ORGANISM: Artificial
<220> FEATURE:
<223> OTHER INFORMATION: Linker

<400> SEQUENCE: 30

Ser Ser Gly Gly Ser Gly Gly Ser Gly Gly Ser Gly Gly Ser Gly Gly
1               5                   10                  15

Ser Gly Gly Ser Gly Gly Ser Gly Ser
            20                  25

```
<210> SEQ ID NO 31
<211> LENGTH: 31
<212> TYPE: PRT
<213> ORGANISM: Artificial
<220> FEATURE:
<223> OTHER INFORMATION: Linker

<400> SEQUENCE: 31

Ser Ser Asn Gly Ser Gly Gly Ser Gly Gly Ser Gly Gly Ser Asn Gly
1               5                   10                  15

Ser Gly Gly Ser Gly Gly Ser Gly Gly Ser Gly Gly Asn Gly Ser
            20                  25                  30

<210> SEQ ID NO 32
<211> LENGTH: 17
<212> TYPE: PRT
<213> ORGANISM: Artificial
<220> FEATURE:
<223> OTHER INFORMATION: Linker

<400> SEQUENCE: 32

Arg Ala Glu Thr Val Phe Pro Asp Val Asp Tyr Val Asn Ser Thr Glu
1               5                   10                  15

Ala

<210> SEQ ID NO 33
<211> LENGTH: 14
<212> TYPE: PRT
<213> ORGANISM: Artificial
<220> FEATURE:
<223> OTHER INFORMATION: Linker

<400> SEQUENCE: 33

Arg Ala Glu Thr Val Phe Pro Asp Val Asp Tyr Val Asn Ser
1               5                   10

<210> SEQ ID NO 34
<211> LENGTH: 17
<212> TYPE: PRT
<213> ORGANISM: Artificial
<220> FEATURE:
<223> OTHER INFORMATION: Linker

<400> SEQUENCE: 34

Arg Ala Glu Ala Val Phe Pro Asp Val Asp Tyr Val Asn Ser Thr Glu
1               5                   10                  15

Ala

<210> SEQ ID NO 35
<211> LENGTH: 19
<212> TYPE: PRT
<213> ORGANISM: Artificial
<220> FEATURE:
<223> OTHER INFORMATION: Linker

<400> SEQUENCE: 35

Arg Ala Glu Ala Val Phe Pro Asp Val Asp Tyr Val Asn Ser Thr Glu
1               5                   10                  15

Ala Gly Ser

<210> SEQ ID NO 36
<211> LENGTH: 19
<212> TYPE: PRT
<213> ORGANISM: Artificial
<220> FEATURE:
```

<223> OTHER INFORMATION: Linker

<400> SEQUENCE: 36

Ser Val Ser Gln Thr Ser Lys Leu Thr Arg Ala Glu Thr Val Phe Pro
1               5                   10                  15

Asp Val Asp

<210> SEQ ID NO 37
<211> LENGTH: 21
<212> TYPE: PRT
<213> ORGANISM: Artificial
<220> FEATURE:
<223> OTHER INFORMATION: Linker

<400> SEQUENCE: 37

Ser Val Ser Gln Thr Ser Lys Leu Thr Arg Ala Glu Thr Val Phe Pro
1               5                   10                  15

Asp Val Asp Gly Ser
            20

<210> SEQ ID NO 38
<211> LENGTH: 19
<212> TYPE: PRT
<213> ORGANISM: Artificial
<220> FEATURE:
<223> OTHER INFORMATION: Linker

<400> SEQUENCE: 38

Ser Val Ser Gln Thr Ser Lys Leu Thr Arg Ala Glu Thr Val Phe Pro
1               5                   10                  15

Asp Val Asp

<210> SEQ ID NO 39
<211> LENGTH: 21
<212> TYPE: PRT
<213> ORGANISM: Artificial
<220> FEATURE:
<223> OTHER INFORMATION: Linker

<400> SEQUENCE: 39

Ser Val Ser Gln Thr Ser Lys Leu Thr Arg Ala Glu Thr Val Phe Pro
1               5                   10                  15

Asp Val Asp Gly Ser
            20

<210> SEQ ID NO 40
<211> LENGTH: 22
<212> TYPE: PRT
<213> ORGANISM: Artificial
<220> FEATURE:
<223> OTHER INFORMATION: Linker

<400> SEQUENCE: 40

Ser Val Ser Gln Thr Ser Lys Leu Thr Arg Ala Glu Thr Val Phe Pro
1               5                   10                  15

Asp Val Asp Asn Gly Ser
            20

<210> SEQ ID NO 41
<211> LENGTH: 19
<212> TYPE: PRT
<213> ORGANISM: Artificial
<220> FEATURE:
<223> OTHER INFORMATION: Linker

```
<400> SEQUENCE: 41

Ser Val Ser Gln Thr Ser Lys Leu Thr Arg Gly Glu Thr Val Phe Pro
1               5                   10                  15

Asp Val Asp

<210> SEQ ID NO 42
<211> LENGTH: 19
<212> TYPE: PRT
<213> ORGANISM: Artificial
<220> FEATURE:
<223> OTHER INFORMATION: Linker

<400> SEQUENCE: 42

Ser Val Ser Gln Thr Ser Lys Leu Thr Arg Thr Glu Thr Val Phe Pro
1               5                   10                  15

Asp Val Asp

<210> SEQ ID NO 43
<211> LENGTH: 19
<212> TYPE: PRT
<213> ORGANISM: Artificial
<220> FEATURE:
<223> OTHER INFORMATION: Linker

<400> SEQUENCE: 43

Ser Val Ser Gln Thr Ser Lys Leu Thr Arg Ser Glu Thr Val Phe Pro
1               5                   10                  15

Asp Val Asp

<210> SEQ ID NO 44
<211> LENGTH: 19
<212> TYPE: PRT
<213> ORGANISM: Artificial
<220> FEATURE:
<223> OTHER INFORMATION: Linker

<400> SEQUENCE: 44

Ser Val Ser Gln Thr Ser Lys Leu Thr Arg Leu Glu Thr Val Phe Pro
1               5                   10                  15

Asp Val Asp

<210> SEQ ID NO 45
<211> LENGTH: 19
<212> TYPE: PRT
<213> ORGANISM: Artificial
<220> FEATURE:
<223> OTHER INFORMATION: Linker

<400> SEQUENCE: 45

Ser Val Ser Gln Thr Ser Lys Leu Thr Arg Thr Glu Ala Val Phe Pro
1               5                   10                  15

Asp Val Asp

<210> SEQ ID NO 46
<211> LENGTH: 19
<212> TYPE: PRT
<213> ORGANISM: Artificial
<220> FEATURE:
<223> OTHER INFORMATION: Linker

<400> SEQUENCE: 46

Ser Val Ser Gln Thr Ser Lys Leu Thr Arg Gly Glu Ala Val Phe Pro
1               5                   10                  15
```

Asp Val Asp

<210> SEQ ID NO 47
<211> LENGTH: 14
<212> TYPE: PRT
<213> ORGANISM: Artificial
<220> FEATURE:
<223> OTHER INFORMATION: Linker

<400> SEQUENCE: 47

Ser Lys Leu Thr Arg Ala Glu Thr Val Phe Pro Asp Val Asp
1               5                   10

<210> SEQ ID NO 48
<211> LENGTH: 14
<212> TYPE: PRT
<213> ORGANISM: Artificial
<220> FEATURE:
<223> OTHER INFORMATION: Linker

<400> SEQUENCE: 48

Gln Ser Phe Asn Asp Phe Thr Arg Val Val Gly Gly Glu Asp
1               5                   10

<210> SEQ ID NO 49
<211> LENGTH: 16
<212> TYPE: PRT
<213> ORGANISM: Artificial
<220> FEATURE:
<223> OTHER INFORMATION: Linker

<400> SEQUENCE: 49

Gln Ser Phe Asn Asp Phe Thr Arg Val Val Gly Gly Glu Asp Gly Ser
1               5                   10                  15

<210> SEQ ID NO 50
<211> LENGTH: 14
<212> TYPE: PRT
<213> ORGANISM: Artificial
<220> FEATURE:
<223> OTHER INFORMATION: Linker

<400> SEQUENCE: 50

Gln Ser Phe Asn Asp Phe Thr Arg Thr Val Gly Gly Glu Asp
1               5                   10

<210> SEQ ID NO 51
<211> LENGTH: 14
<212> TYPE: PRT
<213> ORGANISM: Artificial
<220> FEATURE:
<223> OTHER INFORMATION: Linker

<400> SEQUENCE: 51

Gln Ser Phe Asn Asp Phe Thr Arg Leu Val Gly Gly Glu Asp
1               5                   10

<210> SEQ ID NO 52
<211> LENGTH: 14
<212> TYPE: PRT
<213> ORGANISM: Artificial
<220> FEATURE:
<223> OTHER INFORMATION: Linker

<400> SEQUENCE: 52

Gln Ser Phe Asn Asp Phe Thr Arg Gly Val Gly Gly Glu Asp
1               5                   10

```
<210> SEQ ID NO 53
<211> LENGTH: 17
<212> TYPE: PRT
<213> ORGANISM: Artificial
<220> FEATURE:
<223> OTHER INFORMATION: Linker

<400> SEQUENCE: 53

Gln Ser Phe Asn Asp Phe Thr Arg Val Val Gly Gly Glu Asp Asn Gly
1               5                   10                  15

Ser

<210> SEQ ID NO 54
<211> LENGTH: 15
<212> TYPE: PRT
<213> ORGANISM: Artificial
<220> FEATURE:
<223> OTHER INFORMATION: Linker

<400> SEQUENCE: 54

Gln Ser Phe Asn Asp Phe Thr Arg Val Val Gly Gly Glu Asp Asn
1               5                   10                  15

<210> SEQ ID NO 55
<211> LENGTH: 7
<212> TYPE: PRT
<213> ORGANISM: Artificial
<220> FEATURE:
<223> OTHER INFORMATION: Linker

<400> SEQUENCE: 55

Arg Ile Val Gly Gly Gln Glu
1               5

<210> SEQ ID NO 56
<211> LENGTH: 7
<212> TYPE: PRT
<213> ORGANISM: Artificial
<220> FEATURE:
<223> OTHER INFORMATION: Linker

<400> SEQUENCE: 56

Arg Leu Val Gly Gly Gln Glu
1               5

<210> SEQ ID NO 57
<211> LENGTH: 7
<212> TYPE: PRT
<213> ORGANISM: Artificial
<220> FEATURE:
<223> OTHER INFORMATION: Linker

<400> SEQUENCE: 57

Arg Thr Val Gly Gly Gln Glu
1               5

<210> SEQ ID NO 58
<211> LENGTH: 7
<212> TYPE: PRT
<213> ORGANISM: Artificial
<220> FEATURE:
<223> OTHER INFORMATION: Linker

<400> SEQUENCE: 58

Arg Val Val Gly Gly Gln Glu
1               5
```

```
<210> SEQ ID NO 59
<211> LENGTH: 7
<212> TYPE: PRT
<213> ORGANISM: Artificial
<220> FEATURE:
<223> OTHER INFORMATION: Linker

<400> SEQUENCE: 59

Arg Ala Val Gly Gly Gln Glu
1               5

<210> SEQ ID NO 60
<211> LENGTH: 7
<212> TYPE: PRT
<213> ORGANISM: Artificial
<220> FEATURE:
<223> OTHER INFORMATION: Linker

<400> SEQUENCE: 60

Arg Gly Val Gly Gly Gln Glu
1               5

<210> SEQ ID NO 61
<211> LENGTH: 16
<212> TYPE: PRT
<213> ORGANISM: Artificial
<220> FEATURE:
<223> OTHER INFORMATION: Linker

<400> SEQUENCE: 61

Pro Glu Arg Gly Asp Asn Asn Leu Thr Arg Ile Val Gly Gly Gln Glu
1               5                   10                  15

<210> SEQ ID NO 62
<211> LENGTH: 19
<212> TYPE: PRT
<213> ORGANISM: Artificial
<220> FEATURE:
<223> OTHER INFORMATION: Linker

<400> SEQUENCE: 62

Ser Val Ser Gln Thr Ser Lys Leu Thr Arg Ala Glu Thr Val Phe Pro
1               5                   10                  15

Asp Val Asp

<210> SEQ ID NO 63
<211> LENGTH: 15
<212> TYPE: PRT
<213> ORGANISM: Artificial
<220> FEATURE:
<223> OTHER INFORMATION: Linker

<400> SEQUENCE: 63

Gln Ser Phe Asn Asp Phe Thr Arg Val Val Gly Gly Glu Asp Asn
1               5                   10                  15

<210> SEQ ID NO 64
<211> LENGTH: 19
<212> TYPE: PRT
<213> ORGANISM: Artificial
<220> FEATURE:
<223> OTHER INFORMATION: Linker

<400> SEQUENCE: 64

Ser Val Ser Gln Thr Ser Lys Leu Thr Arg Ala Glu Thr Val Phe Pro
1               5                   10                  15
```

Asp Val Asp

<210> SEQ ID NO 65
<211> LENGTH: 16
<212> TYPE: PRT
<213> ORGANISM: Artificial
<220> FEATURE:
<223> OTHER INFORMATION: Linker

<400> SEQUENCE: 65

Lys Arg Asn Ala Ser Lys Pro Gln Gly Arg Ile Val Gly Gly Lys Val
1               5                   10                  15

<210> SEQ ID NO 66
<211> LENGTH: 16
<212> TYPE: PRT
<213> ORGANISM: Artificial
<220> FEATURE:
<223> OTHER INFORMATION: Linker

<400> SEQUENCE: 66

Pro Glu Glu Pro Gln Leu Arg Met Lys Asn Asn Glu Glu Ala Glu Asp
1               5                   10                  15

<210> SEQ ID NO 67
<211> LENGTH: 19
<212> TYPE: PRT
<213> ORGANISM: Artificial
<220> FEATURE:
<223> OTHER INFORMATION: Linker

<400> SEQUENCE: 67

Asp Asn Ser Pro Ser Phe Ile Gln Ile Arg Ser Val Ala Lys Lys His
1               5                   10                  15

Pro Lys Thr

<210> SEQ ID NO 68
<211> LENGTH: 20
<212> TYPE: PRT
<213> ORGANISM: Artificial
<220> FEATURE:
<223> OTHER INFORMATION: Linker

<400> SEQUENCE: 68

Leu Ser Lys Asn Asn Ala Ile Glu Pro Arg Ser Phe Ser Gln Asn Ser
1               5                   10                  15

Arg His Pro Ser
            20

<210> SEQ ID NO 69
<211> LENGTH: 21
<212> TYPE: PRT
<213> ORGANISM: Artificial
<220> FEATURE:
<223> OTHER INFORMATION: Linker

<400> SEQUENCE: 69

Asp Glu Asp Glu Asn Gln Ser Pro Arg Ser Phe Gln Lys Lys Thr Arg
1               5                   10                  15

His Tyr Phe Ile Ala
            20

<210> SEQ ID NO 70
<211> LENGTH: 16
<212> TYPE: PRT
<213> ORGANISM: Artificial

<220> FEATURE:
<223> OTHER INFORMATION: Linker

<400> SEQUENCE: 70

Ser Pro His Val Leu Arg Asn Arg Ala Gln Ser Gly Ser Val Pro Gln
1               5                   10                  15

<210> SEQ ID NO 71
<211> LENGTH: 24
<212> TYPE: PRT
<213> ORGANISM: Artificial
<220> FEATURE:
<223> OTHER INFORMATION: Linker

<400> SEQUENCE: 71

Pro Glu Glu Pro Gln Leu Arg Met Lys Asn Asn Glu Glu Ala Glu Asp
1               5                   10                  15

Tyr Asp Asp Asp Leu Thr Asp Ser
            20

<210> SEQ ID NO 72
<211> LENGTH: 31
<212> TYPE: PRT
<213> ORGANISM: Artificial
<220> FEATURE:
<223> OTHER INFORMATION: Linker

<400> SEQUENCE: 72

Asp Asp Asp Asn Ser Pro Ser Phe Ile Gln Ile Arg Ser Val Ala Lys
1               5                   10                  15

Lys His Pro Lys Thr Trp Val His Tyr Ala Ala Glu Glu Glu Asp
            20                  25                  30

<210> SEQ ID NO 73
<211> LENGTH: 28
<212> TYPE: PRT
<213> ORGANISM: Artificial
<220> FEATURE:
<223> OTHER INFORMATION: Linker

<400> SEQUENCE: 73

Leu Ser Lys Asn Asn Ala Ile Glu Pro Arg Ser Phe Ser Gln Asn Ser
1               5                   10                  15

Arg His Pro Ser Thr Arg Gln Lys Gln Phe Asn Ala
            20                  25

<210> SEQ ID NO 74
<211> LENGTH: 22
<212> TYPE: PRT
<213> ORGANISM: Artificial
<220> FEATURE:
<223> OTHER INFORMATION: Linker

<400> SEQUENCE: 74

Asp Glu Asp Glu Asn Gln Ser Pro Arg Ser Phe Gln Lys Lys Thr Arg
1               5                   10                  15

His Tyr Phe Ile Ala Ala
            20

<210> SEQ ID NO 75
<211> LENGTH: 32
<212> TYPE: PRT
<213> ORGANISM: Artificial
<220> FEATURE:
<223> OTHER INFORMATION: Linker -continued

<400> SEQUENCE: 75

Asp Tyr Gly Met Ser Ser Pro His Val Leu Arg Asn Arg Ala Gln
1               5                   10                  15
Ser Gly Ser Val Pro Gln Phe Lys Lys Val Val Phe Gln Glu Phe Thr
            20                  25                  30

<210> SEQ ID NO 76
<211> LENGTH: 24
<212> TYPE: PRT
<213> ORGANISM: Artificial
<220> FEATURE:
<223> OTHER INFORMATION: Linker

<400> SEQUENCE: 76

Asp Ile Tyr Asp Glu Asp Glu Asn Gln Ser Pro Arg Ser Phe Gln Lys
1               5                   10                  15
Lys Thr Arg His Tyr Phe Ile Ala
            20

<210> SEQ ID NO 77
<211> LENGTH: 17
<212> TYPE: PRT
<213> ORGANISM: Artificial
<220> FEATURE:
<223> OTHER INFORMATION: Linker

<400> SEQUENCE: 77

Asp Asn Ser Pro Ser Phe Ile Gln Ile Arg Ser Val Ala Lys Lys His
1               5                   10                  15
Pro

<210> SEQ ID NO 78
<211> LENGTH: 20
<212> TYPE: PRT
<213> ORGANISM: Artificial
<220> FEATURE:
<223> OTHER INFORMATION: Linker

<400> SEQUENCE: 78

Leu Ser Lys Asn Asn Ala Ile Glu Pro Arg Ser Phe Ser Gln Asn Ser
1               5                   10                  15
Arg His Pro Ser
            20

<210> SEQ ID NO 79
<211> LENGTH: 36
<212> TYPE: PRT
<213> ORGANISM: Artificial
<220> FEATURE:
<223> OTHER INFORMATION: Linker

<400> SEQUENCE: 79

Ser Val Ser Gln Thr Ser Lys Leu Thr Arg Ala Glu Thr Val Phe Pro
1               5                   10                  15
Asp Val Thr Gln Pro Glu Arg Gly Asp Asn Asn Leu Thr Arg Ile Val
            20                  25                  30
Gly Gly Gln Glu
        35

<210> SEQ ID NO 80
<211> LENGTH: 23
<212> TYPE: PRT
<213> ORGANISM: Artificial
<220> FEATURE:

<223> OTHER INFORMATION: Linker

<400> SEQUENCE: 80

Ser Lys Leu Thr Arg Ala Glu Thr Val Phe Pro Asp Asn Asn Leu Thr
1               5                   10                  15

Arg Ile Val Gly Gly Gln Glu
            20

<210> SEQ ID NO 81
<211> LENGTH: 27
<212> TYPE: PRT
<213> ORGANISM: Artificial
<220> FEATURE:
<223> OTHER INFORMATION: Linker

<400> SEQUENCE: 81

Arg Ala Glu Thr Val Phe Pro Asp Val Thr Gln Pro Glu Arg Gly Asp
1               5                   10                  15

Asn Asn Leu Thr Arg Ile Val Gly Gly Gln Glu
            20                  25

<210> SEQ ID NO 82
<211> LENGTH: 22
<212> TYPE: PRT
<213> ORGANISM: Artificial
<220> FEATURE:
<223> OTHER INFORMATION: Linker

<400> SEQUENCE: 82

Arg Ala Glu Thr Val Phe Pro Glu Arg Gly Asp Asn Asn Leu Thr Arg
1               5                   10                  15

Ile Val Gly Gly Gln Glu
            20

<210> SEQ ID NO 83
<211> LENGTH: 32
<212> TYPE: PRT
<213> ORGANISM: Artificial
<220> FEATURE:
<223> OTHER INFORMATION: Linker

<400> SEQUENCE: 83

Ser Val Ser Gln Thr Ser Lys Leu Thr Arg Ala Glu Thr Val Phe Pro
1               5                   10                  15

Asp Val Asp Tyr Val Asn Asn Leu Thr Arg Ile Val Gly Gly Gln Glu
            20                  25                  30

<210> SEQ ID NO 84
<211> LENGTH: 30
<212> TYPE: PRT
<213> ORGANISM: Artificial
<220> FEATURE:
<223> OTHER INFORMATION: Linker

<400> SEQUENCE: 84

Ser Val Ser Gln Thr Ser Lys Leu Thr Arg Ala Glu Thr Val Phe Pro
1               5                   10                  15

Asp Val Asp Asn Asn Leu Thr Arg Ile Val Gly Gly Gln Glu
            20                  25                  30

<210> SEQ ID NO 85
<211> LENGTH: 30
<212> TYPE: PRT
<213> ORGANISM: Artificial
<220> FEATURE:

<223> OTHER INFORMATION: Linker

<400> SEQUENCE: 85

Ser Val Ser Gln Thr Ser Lys Leu Thr Arg Ala Glu Thr Val Phe Pro
1               5                   10                  15

Asp Val Asp Asn Asn Leu Thr Arg Ile Val Gly Gly Gln Glu
            20                  25                  30

<210> SEQ ID NO 86
<211> LENGTH: 52
<212> TYPE: PRT
<213> ORGANISM: Artificial
<220> FEATURE:
<223> OTHER INFORMATION: Linker

<400> SEQUENCE: 86

Ser Val Ser Gln Thr Ser Lys Leu Thr Arg Ala Glu Thr Val Phe Pro
1               5                   10                  15

Asp Val Asp Tyr Val Asn Ser Thr Glu Ala Glu Thr Ile Leu Asp Asn
            20                  25                  30

Ile Thr Gln Ser Thr Gln Ser Phe Asn Asp Phe Thr Arg Val Val Gly
        35                  40                  45

Gly Glu Asp Ala
    50

<210> SEQ ID NO 87
<211> LENGTH: 32
<212> TYPE: PRT
<213> ORGANISM: Artificial
<220> FEATURE:
<223> OTHER INFORMATION: Linker

<400> SEQUENCE: 87

Ser Val Ser Gln Thr Ser Lys Leu Thr Arg Ala Glu Thr Val Phe Pro
1               5                   10                  15

Asp Val Gln Ser Phe Asn Asp Phe Thr Arg Val Val Gly Gly Glu Asp
            20                  25                  30

<210> SEQ ID NO 88
<211> LENGTH: 32
<212> TYPE: PRT
<213> ORGANISM: Artificial
<220> FEATURE:
<223> OTHER INFORMATION: Linker

<400> SEQUENCE: 88

Ser Val Ser Gln Thr Ser Lys Leu Thr Arg Ala Glu Thr Val Phe Pro
1               5                   10                  15

Asp Val Asp Ser Phe Asn Asp Phe Thr Arg Val Val Gly Gly Glu Asp
            20                  25                  30

<210> SEQ ID NO 89
<211> LENGTH: 32
<212> TYPE: PRT
<213> ORGANISM: Artificial
<220> FEATURE:
<223> OTHER INFORMATION: Linker

<400> SEQUENCE: 89

Ser Val Ser Gln Thr Ser Lys Leu Thr Arg Ala Glu Thr Val Phe Pro
1               5                   10                  15

Asp Val Asn Ala Ser Lys Pro Gln Gly Arg Ile Val Gly Gly Lys Val
            20                  25                  30

```
<210> SEQ ID NO 90
<211> LENGTH: 32
<212> TYPE: PRT
<213> ORGANISM: Artificial
<220> FEATURE:
<223> OTHER INFORMATION: Linker

<400> SEQUENCE: 90

Ser Val Ser Gln Thr Ser Lys Leu Thr Arg Ala Glu Thr Val Phe Pro
1               5                   10                  15

Asp Val Asn Ala Ser Lys Pro Gln Gly Arg Leu Val Gly Gly Lys Val
            20                  25                  30

<210> SEQ ID NO 91
<211> LENGTH: 32
<212> TYPE: PRT
<213> ORGANISM: Artificial
<220> FEATURE:
<223> OTHER INFORMATION: Linker

<400> SEQUENCE: 91

Ser Val Ser Gln Thr Ser Lys Leu Thr Arg Ala Glu Thr Val Phe Pro
1               5                   10                  15

Asp Val Asn Ala Ser Lys Pro Gln Gly Arg Thr Val Gly Gly Lys Val
            20                  25                  30

<210> SEQ ID NO 92
<211> LENGTH: 19
<212> TYPE: PRT
<213> ORGANISM: Artificial
<220> FEATURE:
<223> OTHER INFORMATION: Linker

<400> SEQUENCE: 92

Ser Val Ser Gln Thr Ser Lys Leu Thr Arg Ala Glu Thr Val Phe Pro
1               5                   10                  15

Asp Val Asp

<210> SEQ ID NO 93
<211> LENGTH: 666
<212> TYPE: PRT
<213> ORGANISM: Homo Sapiens

<400> SEQUENCE: 93

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
```

-continued

```
            130                 135                 140
Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
                195                 200                 205

Ser Ile Val Asn Glu Lys Trp Ile Val Thr Ala Ala His Cys Val Glu
            210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
                275                 280                 285

Cys Ile Ala Asp Lys Glu Tyr Thr Asn Ile Phe Leu Lys Phe Gly Ser
            290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
                355                 360                 365

His Val Thr Glu Val Glu Gly Thr Ser Phe Leu Thr Gly Ile Ile Ser
            370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr Ser
                405                 410                 415

Val Ser Gln Thr Ser Lys Leu Thr Arg Ala Glu Thr Val Phe Pro Asp
            420                 425                 430

Val Asp Glu Pro Lys Ser Cys Asp Lys Thr His Thr Cys Pro Pro Cys
            435                 440                 445

Pro Ala Pro Glu Leu Leu Gly Gly Pro Ser Val Phe Leu Phe Pro Pro
450                 455                 460

Lys Pro Lys Asp Thr Leu Met Ile Ser Arg Thr Pro Glu Val Thr Cys
465                 470                 475                 480

Val Val Val Asp Val Ser His Glu Asp Pro Glu Val Lys Phe Asn Trp
                485                 490                 495

Tyr Val Asp Gly Val Glu Val His Asn Ala Lys Thr Lys Pro Arg Glu
            500                 505                 510

Glu Gln Tyr Asn Ser Thr Tyr Arg Val Val Ser Val Leu Thr Val Leu
                515                 520                 525

His Gln Asp Trp Leu Asn Gly Lys Glu Tyr Lys Cys Lys Val Ser Asn
            530                 535                 540

Lys Ala Leu Pro Ala Pro Ile Glu Lys Thr Ile Ser Lys Ala Lys Gly
545                 550                 555                 560
```

```
Gln Pro Arg Glu Pro Gln Val Tyr Thr Leu Pro Pro Ser Arg Glu Glu
            565                 570                 575

Met Thr Lys Asn Gln Val Ser Leu Thr Cys Leu Val Lys Gly Phe Tyr
        580                 585                 590

Pro Ser Asp Ile Ala Val Glu Trp Glu Ser Asn Gly Gln Pro Glu Asn
    595                 600                 605

Asn Tyr Lys Thr Thr Pro Pro Val Leu Asp Ser Asp Gly Ser Phe Phe
610                 615                 620

Leu Tyr Ser Lys Leu Thr Val Asp Lys Ser Arg Trp Gln Gln Gly Asn
625                 630                 635                 640

Val Phe Ser Cys Ser Val Met His Glu Ala Leu His Asn His Tyr Thr
            645                 650                 655

Gln Lys Ser Leu Ser Leu Ser Pro Gly Lys
        660                 665

<210> SEQ ID NO 94
<211> LENGTH: 7
<212> TYPE: PRT
<213> ORGANISM: Artificial
<220> FEATURE:
<223> OTHER INFORMATION: Linker

<400> SEQUENCE: 94

Gly Gly Gly Gly Gly Gly Val
1               5

<210> SEQ ID NO 95
<211> LENGTH: 24
<212> TYPE: PRT
<213> ORGANISM: Artificial
<220> FEATURE:
<223> OTHER INFORMATION: Linker

<400> SEQUENCE: 95

Ser Val Ser Gln Thr Ser Lys Leu Thr Arg Ala Glu Thr Val Phe Pro
1               5                   10                  15

Asp Val Asp Gly Ser Gly Gly Ser
            20

<210> SEQ ID NO 96
<211> LENGTH: 18
<212> TYPE: PRT
<213> ORGANISM: Artificial
<220> FEATURE:
<223> OTHER INFORMATION: Linker

<400> SEQUENCE: 96

Ser Val Ser Gln Thr Ser Lys Leu Thr Arg Ala Glu Thr Val Phe Pro
1               5                   10                  15

Asp Val

<210> SEQ ID NO 97
<211> LENGTH: 15
<212> TYPE: PRT
<213> ORGANISM: Artificial
<220> FEATURE:
<223> OTHER INFORMATION: Linker

<400> SEQUENCE: 97

Gln Thr Ser Lys Leu Thr Arg Ala Glu Thr Val Phe Pro Asp Val
1               5                   10                  15

<210> SEQ ID NO 98
```

```
<211> LENGTH: 13
<212> TYPE: PRT
<213> ORGANISM: Artificial
<220> FEATURE:
<223> OTHER INFORMATION: Linker

<400> SEQUENCE: 98

Ser Lys Leu Thr Arg Ala Glu Thr Val Phe Pro Asp Val
1               5                   10

<210> SEQ ID NO 99
<211> LENGTH: 16
<212> TYPE: PRT
<213> ORGANISM: Artificial
<220> FEATURE:
<223> OTHER INFORMATION: Linker

<400> SEQUENCE: 99

Ser Val Ser Gln Thr Ser Lys Leu Thr Arg Ala Glu Thr Val Phe Pro
1               5                   10                  15

<210> SEQ ID NO 100
<211> LENGTH: 15
<212> TYPE: PRT
<213> ORGANISM: Artificial
<220> FEATURE:
<223> OTHER INFORMATION: Linker

<400> SEQUENCE: 100

Ser Val Ser Gln Thr Ser Lys Leu Thr Arg Ala Glu Thr Val Phe
1               5                   10                  15

<210> SEQ ID NO 101
<211> LENGTH: 12
<212> TYPE: PRT
<213> ORGANISM: Artificial
<220> FEATURE:
<223> OTHER INFORMATION: Linker

<400> SEQUENCE: 101

Gln Thr Ser Lys Leu Thr Arg Ala Glu Thr Val Phe
1               5                   10

<210> SEQ ID NO 102
<211> LENGTH: 10
<212> TYPE: PRT
<213> ORGANISM: Artificial
<220> FEATURE:
<223> OTHER INFORMATION: Linker

<400> SEQUENCE: 102

Ser Lys Leu Thr Arg Ala Glu Thr Val Phe
1               5                   10

<210> SEQ ID NO 103
<211> LENGTH: 13
<212> TYPE: PRT
<213> ORGANISM: Artificial
<220> FEATURE:
<223> OTHER INFORMATION: Linker

<400> SEQUENCE: 103

Ser Val Ser Gln Thr Ser Lys Leu Thr Arg Ala Glu Thr
1               5                   10

<210> SEQ ID NO 104
<211> LENGTH: 10
<212> TYPE: PRT
```

```
<213> ORGANISM: Artificial
<220> FEATURE:
<223> OTHER INFORMATION: Linker

<400> SEQUENCE: 104

Gln Thr Ser Lys Leu Thr Arg Ala Glu Thr
1               5                   10

<210> SEQ ID NO 105
<211> LENGTH: 8
<212> TYPE: PRT
<213> ORGANISM: Artificial
<220> FEATURE:
<223> OTHER INFORMATION: Linker

<400> SEQUENCE: 105

Ser Lys Leu Thr Arg Ala Glu Thr
1               5

<210> SEQ ID NO 106
<211> LENGTH: 18
<212> TYPE: PRT
<213> ORGANISM: Artificial
<220> FEATURE:
<223> OTHER INFORMATION: Linker

<400> SEQUENCE: 106

Gln Thr Ser Lys Leu Thr Arg Ala Glu Thr Val Phe Pro Asp Val Asp
1               5                   10                  15

Gly Ser

<210> SEQ ID NO 107
<211> LENGTH: 16
<212> TYPE: PRT
<213> ORGANISM: Artificial
<220> FEATURE:
<223> OTHER INFORMATION: Linker

<400> SEQUENCE: 107

Ser Lys Leu Thr Arg Ala Glu Thr Val Phe Pro Asp Val Asp Gly Ser
1               5                   10                  15

<210> SEQ ID NO 108
<211> LENGTH: 13
<212> TYPE: PRT
<213> ORGANISM: Artificial
<220> FEATURE:
<223> OTHER INFORMATION: Linker

<400> SEQUENCE: 108

Gln Ser Phe Asn Asp Phe Thr Arg Val Val Gly Gly Glu
1               5                   10

<210> SEQ ID NO 109
<211> LENGTH: 18
<212> TYPE: PRT
<213> ORGANISM: Artificial
<220> FEATURE:
<223> OTHER INFORMATION: Linker

<400> SEQUENCE: 109

Pro Glu Arg Gly Asp Asn Asn Leu Thr Arg Ile Val Gly Gly Gln Glu
1               5                   10                  15

Gly Ser

<210> SEQ ID NO 110
```

```
<211> LENGTH: 15
<212> TYPE: PRT
<213> ORGANISM: Artificial
<220> FEATURE:
<223> OTHER INFORMATION: Linker

<400> SEQUENCE: 110

Pro Glu Arg Gly Asp Asn Asn Leu Thr Arg Ile Val Gly Gly Gln
1               5                   10                  15

<210> SEQ ID NO 111
<211> LENGTH: 11
<212> TYPE: PRT
<213> ORGANISM: Artificial
<220> FEATURE:
<223> OTHER INFORMATION: Linker

<400> SEQUENCE: 111

Asp Asn Asn Leu Thr Arg Ile Val Gly Gly Gln
1               5                   10

<210> SEQ ID NO 112
<211> LENGTH: 11
<212> TYPE: PRT
<213> ORGANISM: Artificial
<220> FEATURE:
<223> OTHER INFORMATION: Linker

<400> SEQUENCE: 112

Ala Ser Lys Pro Gln Gly Arg Ile Val Gly Gly
1               5                   10

<210> SEQ ID NO 113
<211> LENGTH: 18
<212> TYPE: PRT
<213> ORGANISM: Artificial
<220> FEATURE:
<223> OTHER INFORMATION: Linker

<400> SEQUENCE: 113

Pro Val Ser Gln Thr Ser Lys Leu Thr Arg Ala Glu Thr Val Phe Pro
1               5                   10                  15

Asp Val

<210> SEQ ID NO 114
<211> LENGTH: 19
<212> TYPE: PRT
<213> ORGANISM: Artificial
<220> FEATURE:
<223> OTHER INFORMATION: Linker

<400> SEQUENCE: 114

Pro Ser Val Ser Gln Thr Ser Lys Leu Thr Arg Ala Glu Thr Val Phe
1               5                   10                  15

Pro Asp Val
```

PROTEOLYTICALLY CLEAVABLE FUSION PROTEINS WITH HIGH MOLAR SPECIFIC ACTIVITY

This application is a continuation-in-part of U.S. application Ser. No. 11/812,016, filed Jun. 14, 2007, which claims priority to U.S. Provisional Application No. 60/819,620, filed Jul. 11, 2006. The application also claims priority to European Patent Application No. 06012262.9, filed Jun. 14, 2006.

The present invention relates to the field of modified therapeutic fusion proteins with increased half-life compared to their non-modified parent therapeutic polypeptides. The invention, for example, relates to coagulation factors fused to half-life enhancing polypeptides (HLEPs), which are connected by linker peptides that are proteolytically cleavable. The cleavage of such linkers liberates the therapeutic polypeptide from activity-compromising steric hindrance caused by the HLEP and thereby allows the generation of fusion proteins, which retain a high molar specific activity of the coagulation factor. When the therapeutic fusion proteins are zymogens, one may use linkers that liberate the therapeutic polypeptide essentially simultaneously with its activation in vivo upon exposure to the corresponding protease(s). Embodiments of the present invention may show a faster inactivation rate of a given coagulation factor once the coagulation factor is activated and the peptide linker is proteolytically cleaved in a coagulation-related mode and/or a faster elimination rate of a given coagulation factor once the coagulation factor is activated and the peptide linker is proteolytically cleaved in a coagulation-related mode, compared to the corresponding fusion protein without cleavable linker.

One aspect of the invention is demonstrated for example by human vitamin K-dependent polypeptides Factor IX, Factor VII, and Factor VIIa. The same concept also may be applied to other coagulation factors. Any half-life enhancing polypeptide (HLEP) may be connected to the therapeutic polypeptide by a cleavable linker peptide. For instance albumin or immunoglobulins or fragments derived therefrom without an antigen binding domain, such as the Fc fragment, may serve as HLEPs. The invention also relates to cDNA sequences coding for the therapeutic polypeptides and derivatives thereof genetically fused to a cDNA coding for HLEPs, such as human serum albumin linked by oligonucleotides that code for cleavable, intervening peptide linkers. Such encoded derivatives may exhibit improved half-life and molar specific activities that are increased in comparison to their non-cleavable counterparts. The invention also relates to recombinant expression vectors containing such cDNA sequences, host cells transformed with such recombinant expression vectors, recombinant polypeptides and derivatives which may have biological activities comparable to the unmodified wild type therapeutic polypeptide, but having improved half-lifes. The invention also relates to processes for the manufacture of such recombinant proteins and their derivatives. The invention also relates to a transfer vector for use in human gene therapy, which comprises such modified DNA sequences, which can be useful to increase half-life in vivo.

Several recombinant, therapeutic polypeptides are commercially available for therapeutic and prophylactic use in humans. The patients in general may benefit from the specific mode of action of the recombinant active ingredients but a disadvantage may be their limited availability due to expensive and complex manufacturing processes. A reduction of the necessary dose or the frequency of administration of such products could improve this situation. A reduced frequency of administration could improve the convenience for the patient and, therefore, also the acceptance of the therapy. Several ideas have been described to attempt to achieve the goal of an increased in vivo half-life after administration. See, e.g. Ballance et al. (WO 01/79271), Sheffield et al. (Sheffield W. P. et al. (2004), Br. J. Haematol. 126: 565-573), WO 2002/04598, WO 2003/059935, WO 2004/081053, WO 2004/101740, WO 2005/001025, WO 91/09125, and WO 03/068934.

Fusions of coagulation factors to half-life enhancing polypeptides have been suggested to lengthen the half-life of coagulation factors administered to patients. However, once a coagulation factor is activated during coagulation either by proteolytic cleavage of the zymogen (like FIX) or by contact of an already proteolytically "pre"-activated factor to a second polypeptide (like FVIIa binding to Tissue Factor), it may no longer be desirable to maintain the long half-life of the now activated coagulation factor, as this might lead to thrombotic complications. This is the case for a wild type coagulation factor such as FVIIa (Aledort L. M., J Thromb Haemost 2(10): 1700-1708 (2004)) and may be even more relevant if the activated factor has an increased half-life. It is therefore one objective of some embodiments of the present invention to provide long-lived coagulation factors, which after activation or after availability of a cofactor have a half-life comparable to that of an unmodified coagulation factor.

Fusions of the coagulation factors to half-life enhancing polypeptides as described in the prior art and as also shown in examples 6 and 7 may suffer in general from a reduced molar specific activity of the fused coagulation factor. Another aspect of the present invention is to provide coagulation factors with enhanced half-life that show increased molar specific activity compared to the corresponding therapeutic fusion protein without a cleavable linker.

Some embodiments of this invention include therapeutic fusion proteins comprising:
  a) a coagulation factor,
  b) a half-life enhancing polypeptide (HLEP) chosen from albumin immunoglobulin, and
  c) a peptide linker, which linker joins the coagulation factor and the half-life enhancing polypeptide;
wherein the peptide linker is cleavable by proteases involved in coagulation or proteases activated by coagulation enzymes, and wherein the therapeutic fusion protein has, in comparison to the respective therapeutic fusion protein linked by a non-cleavable linker having the amino acid sequence GGGGGGV (SEQ ID NO: 94), at least one of the following properties:
  i) an increased molar specific activity in at least one coagulation-related assay,
  ii) an increased inactivation rate of the activated coagulation factor after the peptide linker is proteolytically cleaved in a coagulation-related mode, and
  iii) an increased elimination rate of the activated coagulation factor after the peptide linker is proteolytically cleaved in a coagulation-related mode.

A "coagulation factor," as used herein, includes variants or derivatives thereof, such as genetically engineered or chemically modified variants or active fragments thereof. See below for additional description of examples of "coagulation factors."

"Albumin," as used herein, includes polypeptides of the albumin family of proteins such as human serum albumin and bovine serum albumin, including variants and derivatives thereof, such as genetically engineered or chemically modified albumin variants and fragments of albumin proteins. See below for additional description of examples of "albumin."

"Immunoglobulin," as used herein, includes variants and derivatives of immunoglobulin proteins, such as genetically engineered or chemically modified immunoglobulin variants and fragments of immunoglobulin, for example, an Fc fragment or other fragment not containing an antigen binding domain. See below for additional description of examples of "immunoglobulin."

As a consequence of the cleavable linker, after cleavage of the peptide linker in a coagulation-related mode the coagulation factor more closely resembles the behaviour of the native, non-fused factor and does not show an increased half-life of the active factor with potentially prothrombotic effect.

"Proteolytic cleavage in a coagulation-related mode," as used herein, means any proteolytic cleavage that occurs as a consequence of the activation of at least one coagulation factor or coagulation cofactor.

The phrase "activated coagulation factor after the peptide linker is proteolytically cleaved in a coagulation-related mode," as used herein means that the coagulation factor is either activated almost in parallel to the proteolytic cleavage of the linker peptide, or that the coagulation factor was already activated before the proteolytic cleavage of the linker peptide. Activation may occur, for example by proteolytic cleavage of the coagulation factor or by binding to a cofactor.

A further aspect of the present invention is to provide therapeutic fusion proteins comprising:
a) a coagulation factor,
b) a half-life enhancing polypeptide (HLEP) chosen from albumin and immunoglobulin, and
c) a peptide linker which joins the coagulation factor and the half-life enhancing polypeptide;
wherein the peptide linker is cleavable by proteases involved in coagulation or activated by coagulation enzymes, and wherein the therapeutic fusion protein has, in comparison to the respective therapeutic fusion protein linked by a non-cleavable linker having the amino acid sequence GGGGGGV (SEQ ID NO: 94), at least one of the following properties:
i) an increased molar specific activity in at least one coagulation-related assay,
ii) an increased inactivation rate of the activated coagulation factor after the peptide linker is proteolytically cleaved in a coagulation-related mode,
iii) an increased elimination rate of the activated coagulation factor after the peptide linker is proteolytically cleaved in a coagulation-related mode, and
iv) an enhanced in vivo recovery as compared to the in vivo recovery of the unmodified coagulation factor.

Some embodiments include therapeutic fusion proteins which have an enhanced in vivo recovery compared to the unmodified coagulation factor by at least 10%, for example, by at least 25% or by 40% or more.

Exemplary coagulation factors are vitamin-K dependent coagulation factors, FVIIa, and FIX, and fragments and variants thereof, such as genetically engineered or chemically modified variants or fragments, such as are described in more detail below.

HLEPs may be albumin and fragments or variants thereof and immunoglobulins including fragments and variants thereof, as described above, and in more detail, below.

The peptide linker in some embodiments may comprise a sequence of the therapeutic polypeptide to be administered or a variant thereof, which should result in a decreased risk of neoantigenic properties (formation of a novel potentially immunogenic epitope due to the occurrence of a peptide within the therapeutic antigen which does not exist in human proteins) of the expressed fusion protein. Also in case the therapeutic protein is a zymogen (e.g. needs to be proteolytically activated) the kinetics of the peptide linker cleavage may more closely reflect the coagulation-related activation kinetics of the zymogen. Thus, in some embodiments, a zymogen and a corresponding peptide linker are activated and respectively cleaved, with comparable kinetics. For this reason, embodiments of the present invention also relate to fusion proteins of a zymogen and a HLEP, where the kinetics of the linker cleavage by relevant proteases are not delayed by more than a factor of 3, such as not by more than a factor of 2, compared to the kinetics of the zymogen activation.

In another embodiment, the peptide linker comprises cleavage sites for more than one protease. This can be achieved, for example, by a peptide linker that can be cleaved at the same position by different proteases or by a peptide linker that provides two or more different cleavage sites. This may be advantageous circumstances where the therapeutic fusion protein must be activated by proteolytic cleavage to achieve enzymatic activity and where different proteases may contribute to this activation step. This is the case, for example, upon activation of FIX, which can either be achieved by FXIa or by FVIIa/Tissue Factor (TF).

Some embodiments of the invention are therapeutic fusion proteins wherein the peptide linker is cleavable by the protease that normally activates the coagulation factor in vivo, thereby ensuring that the cleavage of the linker is linked to the activation of the coagulation factor at a site at which coagulation occurs.

Other exemplary therapeutic fusion proteins according to the invention are those wherein the linker is cleavable by the coagulation factor which is part of the therapeutic fusion protein once it is activated, thus also ensuring that cleavage of the fusion protein is connected with a coagulatory event.

Other exemplary therapeutic fusion proteins according to the invention are those wherein the linker is cleavable by a protease, which itself is activated directly or indirectly by the activity of the coagulation factor which is part of the therapeutic fusion protein, thus also ensuring that cleavage of the fusion protein is connected with a coagulatory event.

One class of therapeutic fusion proteins included in this invention comprises those wherein the linker is cleavable by FXIa and/or by FVIIa/TF and the coagulation factor is FIX.

For example, embodiments of the invention include fusion proteins comprising the vitamin K-dependent polypeptide Factor IX, cleavable linkers, and albumin as the HLEP, as well as their corresponding cDNA sequences. The invention also relates to cDNA sequences coding for any other coagulation factors which can be proteolytically activated or that are involved in the activation of other zymogens or polypeptides. In some embodiments, these cDNAs are genetically fused to cDNA sequences coding for human serum albumin or other HLEPs, and are linked by oligonucleotides that code for intervening, cleavable peptide linkers. The expressed therapeutic fusion proteins may exhibit molar specific activities which are increased in comparison to their non-cleavable counterparts. The invention also relates to recombinant expression vectors containing such fused cDNA sequences, host cells transformed with such recombinant expression vectors, recombinant therapeutic fusion proteins and derivatives that may have biological activities almost comparable to the unmodified wild type therapeutic polypeptides but having improved in vivo half-life. The invention also relates to processes for the manufacture of the recombinant polypeptides of the invention and their derivatives. The invention also relates to a transfer vector for use in human gene therapy, which comprises such modified DNA sequences useful to increase product levels in vivo.

Some therapeutic fusion proteins according to the invention have a molar specific activity, in particular a molar specific activity in at least one coagulation-related assay, that is at least 25% increased compared to that of the corresponding therapeutic fusion protein without a cleavable linker. Other therapeutic fusion proteins have a molar specific activity that is increased by at least 50%, or by at least 100%, in at least one of the different coagulation-related assays available, compared to that of the corresponding therapeutic fusion protein without a cleavable linker, such as one with the non-cleavable sequence GGGGGGV (SEQ ID NO: 94).

Additional embodiments of the present invention are therapeutic fusion proteins wherein the inactivation rate of the activated coagulation factor after cleavage of the peptide linker which links the coagulation factor to the half-life enhancing polypeptide is increased by at least 10% as compared to the inactivation rate of the activated coagulation factor in a corresponding therapeutic fusion protein without a cleavable linker. Other embodiments are therapeutic fusion proteins in which the inactivation rate is increased by at least 25%, or by at least 50% as compared to the inactivation rate of the activated coagulation factor in a corresponding therapeutic fusion protein without a cleavable linker, such as one with the non-cleavable sequence GGGGGGV (SEQ ID NO: 94).

Additional embodiments of the present invention are therapeutic fusion proteins wherein the elimination rate of the coagulation factor after cleavage of the peptide linker that links the coagulation factor to the half-life enhancing polypeptide is increased by at least 10% as compared to the elimination rate of the coagulation factor in a corresponding therapeutic fusion protein without a cleavable linker. Other embodiments are therapeutic fusion proteins in which the elimination rate is increased by at least 25%, or by at least 50% as compared to the elimination rate of the coagulation factor in a corresponding therapeutic fusion protein without a cleavable linker, such as one with the non-cleavable sequence GGGGGGV (SEQ ID NO: 94).

Vitamin K-Dependent Polypeptides

Vitamin K-dependent polypeptides as one group of the therapeutic polypeptides are polypeptides that are γ-carboxylated enzymatically in the liver using vitamin K as a cofactor. Such vitamin K-dependent polypeptides e.g. include Factors II, VII, IX, X, Protein C, Protein S, GAS6, and Protein Z.

Human FIX

Human FIX, one member of the group of vitamin K-dependent polypeptides, is a single-chain glycoprotein with a molecular weight of 57 kDa, which is secreted by liver cells into the blood stream as an inactive zymogen of 415 amino acids. It contains 12 γ-carboxy-glutamic acid residues localized in the N-terminal Gla-domain of the polypeptide. The Gla residues require vitamin K for their biosynthesis. Following the Gla domain there are two epidermal growth factor domains, an activation peptide, and a trypsin-type serine protease domain. Further posttranslational modifications of FIX encompass hydroxylation (Asp 64), N-(Asn157 and Asn167) as well as O-type glycosylation (Ser53, Ser61, Thr159, Thr169, and Thr172), sulfation (Tyr155), and phosphorylation (Ser158). FIX is converted to its active form, Factor IXa, by proteolysis of the activation peptide at Arg145-Ala146 and Arg180-Val181 leading to the formation of two polypeptide chains, an N-terminal light chain (18 kDa) and a C-terminal heavy chain (28 kDa), which are held together by one disulfide bridge. Activation cleavage of Factor IX can be achieved in vitro e.g. by Factor XIa or Factor VIIa/TF. Factor IX is present in human plasma in a concentration of 5-10 μg/ml. Terminal plasma half-life of Factor IX in humans was found to be about 15 to 18 hours (White G C et al. 1997. Recombinant factor IX. Thromb Haemost. 78: 261-265; Ewenstein B M et al. 2002. Pharmacokinetic analysis of plasma-derived and recombinant F IX concentrates in previously treated patients with moderate or severe hemophilia B. Transfusion 42:190-197).

Hemophilia B is caused by non-functional or missing Factor IX and is treated with Factor IX concentrates from plasma or a recombinant form of Factor IX. As haemophilia B patients often receive at least biweekly prophylactic administrations of Factor IX to avoid spontaneous bleedings, it is desirable to increase the intervals of time between administrations by increasing the half-life of the Factor IX product applied. An improvement in plasma half-life may bring significant benefit to the patient. Up to now no pharmaceutical preparation of a Factor IX with improved plasma half-life is commercially available nor have any data been published showing F IX variants with prolonged in vivo half-life and almost unchanged molar specific activity in coagulation-related assays. Therefore, a great medical need still exists to develop forms of Factor IX which have a longer functional half-life in vivo.

Factor VII and Factor VIIa

FVII is a single-chain glycoprotein with a molecular weight of 50 kDa, which is secreted by liver cells into the blood stream as an inactive zymogen of 406 amino acids. FVII is converted to its active form Factor VIIa, by proteolysis of the single peptide bond at Arg152-Ile153 leading to the formation of two polypeptide chains, a N-terminal light chain (24 kDa) and a C-terminal heavy chain (28 kDa), which are held together by one disulfide bridge. In contrast to other vitamin K-dependent coagulation factors, no activation peptide is cleaved off during activation. Activation cleavage of Factor VII can be achieved in vitro, for example, by Factor Xa, Factor IXa, Factor VIIa, Factor XIIa, Factor Seven Activating Protease (FSAP), and thrombin. Mollerup et al. (Biotechnol. Bioeng. (1995) 48: 501-505) reported that some cleavage also occurs in the heavy chain at Arg290 and/or Arg315.

Factor VII is present in plasma in a concentration of 500 ng/ml. About 1% or 5 ng/ml of Factor VII is present as activated Factor VIIa. The terminal plasma half-life of Factor VII was found to be about 4 hours and that of Factor VIIa about 2 hours.

By administering supraphysiological concentrations of Factor VIIa hemostasis can be achieved bypassing the need for Factor VIIIa and Factor IXa. The cloning of the cDNA for Factor VII (U.S. Pat. No. 4,784,950) made it possible to develop activated Factor VII as a pharmaceutical. Factor VIIa was successfully administered for the first time in 1988. Ever since the number of indications of Factor VIIa has grown steadily showing a potential to become an universal hemostatic agent to stop bleeding (Erhardtsen, 2002). However, the short terminal half-life of Factor VIIa of approximately 2 hours and reduced in vivo recovery may be limiting its application. Therefore, a great medical need still exists to develop forms of Factor VIIa which have an improved half-life but otherwise almost uncompromised molar specific activity, inactivation kinetics, and/or elimination kinetics after start of coagulation.

Therapeutic Fusion Proteins

"Therapeutic fusion proteins" or "fusion proteins" as used herein are coagulation factors fused to a half-life enhancing polypeptide such that, upon administration to a human or other animal, may produce a prophylactic or therapeutic effect. These therapeutic fusion proteins may be administered to a human or other animal via, for example, intravenous, intramuscular, subcutaneous, oral, topical, parenteral or other routes. In addition, gene therapy protocols may be used which involve administration of a polynucleotide encoding the fusion protein or a composition comprising that polynucleotide, such as a plasmid or vector or host cell. Specific classes of therapeutic fusion proteins described, i.e. by the examples below, are coagulation factors, such as vitamin K-dependent polypeptides, linked to half-life enhancing polypeptides, such as albumin and immunoglobulin. The expression "therapeutic fusion protein" is used interchangeably with "fusion protein".

Half-Life Enhancing Polypeptide (HLEP)

Albumin and immunoglobulin have been described above as examples of half-life enhancing polypeptides (HLEPs). The terms "human serum albumin" (HSA) and "human albumin" (HA) are used interchangeably in this application. The terms "albumin" and "serum albumin" are broader, and encompass human serum albumin as well as albumin from other species, and fragments and variants thereof.

"Albumin," as used herein, includes polypeptides of the albumin family of proteins. As used herein, "albumin" refers collectively to albumin polypeptide or amino acid sequence, or an albumin fragment or variant having one or more functional activities (e.g., biological activities) of albumin. Examples include human serum albumin and bovine serum albumin, including variants and derivatives thereof, such as genetically engineered or chemically modified albumin variants and fragments of albumin proteins. For example, "albumin" refers to human albumin or fragments thereof, such as the mature form of human albumin as shown in SEQ ID NO:1 herein or albumin from other vertebrates or fragments thereof, or analogs or variants of these molecules or fragments thereof.

The albumin portion of the albumin fusion proteins may comprise the full length of, for instance, the HA sequence as described above, or may include one or more fragments thereof that are capable of stabilizing or prolonging the therapeutic activity. Such fragments may be of 10 or more amino acids in length or may include about 15, 20, 25, 30, 50, or more contiguous amino acids from the HA sequence or may include part or all of specific domains of HA.

The albumin portion of the albumin fusion proteins of the invention may comprise a variant or derivative or analog of normal HA, either natural or artificial. The therapeutic polypeptide portion of the fusion proteins of the invention may also comprise variants of the corresponding therapeutic polypeptides as described herein.

The terms "variants" "derivatives" and "analogs", throughout this application, when applied to any protein disclosed herein, each include, for example, insertions, deletions, and substitutions, either conservative or non-conservative, either natural or artificial (i.e. engineered), where such changes do not substantially alter the active site, or a fragment, such as an active domain that confers the therapeutic activities of the therapeutic polypeptides, or chemical modifications that also allow for therapeutic activity. Examples include, for instance coagulation factors, albumin, or immunoglobulins that are 80%, 85%, 90%, and 95% identical in sequence to a wild-type, human coagulation factor, albumin, or immunoglobulin sequence.

In particular, the albumin fusion proteins of the invention may include naturally occurring polymorphic variants of human albumin and fragments of human albumin. The albumin may be derived from any vertebrate, especially any mammal, for example human, cow, sheep, or pig. Non-mammalian albumins include, but are not limited to, hen and salmon. The albumin portion of the albumin-linked polypeptide may be from a different animal than the therapeutic polypeptide portion.

Generally speaking, an albumin fragment or variant encompassed within the term "albumin" will be at least 10, for example at least 40, or more than 70 amino acids long. That albumin variant may comprise at least one whole domain of albumin or fragments of said domains, for example domains 1 (amino acids 1-194 of SEQ ID NO:1), 2 (amino acids 195-387 of SEQ ID NO:1), 3 (amino acids 388-585 of SEQ ID NO:1), 1+2 (1-387 of SEQ ID NO:1), 2+3 (195-585 of SEQ ID NO:1) or 1+3 (amino acids 1-194 of SEQ ID NO:1+amino acids 388-585 of SEQ ID NO:1). Each domain is itself made up of two homologous subdomains namely 1-105, 120-194, 195-291, 316-387, 388-491 and 512-585, with flexible inter-subdomain linker regions comprising residues Lys106 to Glu119, Glu292 to Val315, and Glu492 to Ala511.

The albumin portion of an albumin fusion protein of the invention may comprise at least one subdomain or domain of HA or conservative modifications thereof.

All fragments and variants of albumin are encompassed by the invention as fusion partners of a coagulation factor as long as they lead to a half-life extension of the therapeutic fusion protein in plasma of at least 25% as compared to the non-fused coagulation factor.

The albumin family of proteins, included within the term "albumin" used herein, comprise evolutionarily related serum transport proteins, for example, albumin, alpha-fetoprotein (AFP; Beattie & Dugaiczyk 1982. Gene 20:415-422), afamin (AFM; Lichenstein et al. 1994. J. Biol. Chem. 269: 18149-18154) and vitamin D binding protein (DBP; Cooke & David 1985. J. Clin. Invest. 76:2420-2424). Alpha-fetoprotein has been claimed to enhance the half-life of an attached therapeutic polypeptide in vivo (WO 2005/024044). Their genes represent a multigene cluster with structural and functional similarities mapping to the same chromosomal region in humans, mice and rat. The structural similarity of those albumin family members suggests their usability as HLEPs. Some embodiments of the invention, therefore, may use such albumin family members, or fragments and variants thereof as defined above, as HLEPs.

Albumin family members encompassed within the term "albumin" herein also comprise the full length of the respective proteins AFP, AFM and DBP, or may include one or more fragments thereof that are capable of stabilizing or prolonging the therapeutic activity. Such fragments may be of 10 or more amino acids in length or may include about 15, 20, 25, 30, 50, or more contiguous amino acids of the respective protein sequence or may include part or all of specific domains of the respective protein, as long as the HLEP fragments provide a half-life extension of at least 25% as compared to the non-fused coagulation factor. Albumin family members of the therapeutic fusion proteins of the invention may also include naturally occurring polymorphic variants of AFP, AFM and DBP.

The term "immunoglobulin" as used herein, encompasses, for instance, IgG and IgG-fragments, which may also be used as HLEPs, as long as the corresponding HLEP fragments provide a half-life extension of at least 25% as compared to the non-fused coagulation factor. The therapeutic polypeptide portion may be connected to the IgG or the IgG fragments via a cleavable linker that allows high molar specific activities of the fusion protein. For example, fusion proteins comprising FVII or VIIa and IgG or fragments thereof may be prepared. A linker sequence of the present invention liberating FVII (FVIIa) molecules upon cleavage by a protease of the coagulation cascade such as, e.g., FXIa, FXa, or FIXa could be able to elevate the clotting activity of the constructs to an activity level comparable to the monomer/dimer or even higher. A FIX-Fc fusion protein with cleavable linker is exemplarily shown in SEQ ID NO:93. Cleavable linkers such as those shown in table 3a and 3b may also be applied in such embodiments.

The invention also relates to fusion proteins comprising linking a coagulation factor, including, for example, a fragment or variant thereof, to the N- or C-terminus of a HLEP, including a fragment or variant thereof, such that an intervening cleavable peptide linker is introduced between the therapeutic polypeptide and the HLEP such that the fusion protein formed has an increased in vivo half-life compared to the coagulation factor which has not been linked to a HLEP and that the fusion protein has an at least 25% higher molar specific activity compared to the corresponding fusion protein with non-cleavable linker in at least one of the different coagulation-related assays available.

"Coagulation factor" as used in this application includes, but is not limited to, polypeptides consisting of Factor IX, Factor VII, Factor VIII, von Willebrand Factor, Factor V, Factor X, Factor XI, Factor XII, Factor XIII, Factor I, Factor II (Prothrombin), Protein C, Protein S, GAS6, or Protein Z as well as their activated forms. A "coagulation factor," as used herein, also includes variants or derivatives thereof, such as genetically engineered or chemically modified variants or active fragments thereof. For instance, useful therapeutic polypeptides may be wild-type polypeptides or may contain mutations. Degree and location of glycosylation or other post-translation modifications may vary depending on the chosen host cells and the nature of the host cellular environment. When referring to specific amino acid sequences, post-translational modifications of such sequences are encompassed in this application.

"Coagulation factor" within the above definition includes polypeptides that have the natural amino acid sequence including any natural polymorphisms. It also includes polypeptides with a slightly modified amino acid sequence, for instance, a modified N-terminal or C-terminal end including terminal amino acid deletions or additions, as long as those polypeptides substantially retain the activity of the respective therapeutic polypeptide. Variants included may differ in one or more amino acid residues from the wild type sequence. Examples of such differences may include truncation of the N- and/or C-terminus by one or more amino acid residues (e.g. 1 to 30 amino acid residues), or addition of one or more extra residues at the N- and/or C-terminus, as well as conservative amino acid substitutions, i.e. substitutions performed within groups of amino acids with similar characteristics, e.g. (1) small amino acids, (2) acidic amino acids, (3) polar amino acids, (4) basic amino acids, (5) hydrophobic amino acids, and (6) aromatic amino acids. Examples of such conservative substitutions are shown in the following table.

TABLE 1

| (1) | Alanine | Glycine | | |
|---|---|---|---|---|
| (2) | Aspartic acid | Glutamic acid | | |
| (3a) | Asparagine | Glutamine | | |
| (3b) | Serine | Threonine | | |
| (4) | Arginine | Histidine | Lysine | |
| (5) | Isoleucine | Leucine | Methionine | Valine |
| (6) | Phenylalanine | Tyrosine | Tryptophane | |

The in vivo half-life of the fusion proteins of the invention, in general determined as terminal half-life or β-half-life, may be at least about 25%, at least about 50%, or more than 100% higher than the in vivo half-life of the non-fused polypeptide.

The fusion proteins of the present invention also have at least a 25%, and may have at least a 50% or at least 100% increased molar specific activity compared to the corresponding fusion proteins without cleavable linkers.

The "molar specific activity" (or molar specific coagulation-related activity as considered here in particular) in this regard is defined for purposes herein as the activity expressed per mole (or e.g. nmole) of the therapeutic polypeptide or therapeutic fusion protein of interest. Calculation of the molar specific activity allows a direct comparison of the activity of the different constructs that is not affected by the different molecular weights or optical densities of the polypeptides studied. The molar specific activity may be calculated as exemplified in table 2 below for FIX and a FIX-HSA fusion protein.

TABLE 2

Calculation of molar specific activity as shown for a purified FIX-HSA fusion protein

| Product | $OD_{(280\,nm,\,1\%)}$ | MW | Activity/Vol/$OD_{280}$ (IU/L/$OD_{280}$) | Molar optical density ($OD_{(280)}$) at 1 mol/L) | Calculation of molar specific activity (IU/mol) |
|---|---|---|---|---|---|
| FIX | 13.3 [1] | 57 000 | determined for product | 75810 (=MW × $OD_{(280,\,1\%)}$/10) | =(Activity/Vol/$OD_{280}$) × ($OD_{280}$ at 1 mol/L) |
| HSA | 5.7 [2] | 66 300 | | 37791 (=MW × $OD_{(280,\,1\%)}$/10) | |
| FIX-HSA | | | determined for product | 113601 (=sum of molar optical density of FIX and HSA) | =(Activity/Vol/$OD_{280}$) × ($OD_{280}$ at 1 mol/L) |

[1] R. G. Di Scipio et al., Biochem. 16: 698-706 (1977)
[2] C. Chaudhury et al, J. Exp. Med. 197(3): 315-322 (2003)

In order to determine a molar specific coagulation-related activity, any assay may be used that determines enzymatic or cofactor activities that are relevant to the coagulation process.

Therefore "coagulation-related assays" in the sense of the invention comprise any assay which determines enzymatic or cofactor activities that are of relevance in the coagulation process or that are able to determine that either the intrinsic or the extrinsic coagulation cascade has been activated. The "coagulation-related" assay thus may be direct coagulation assays like aPTT, PT, or the thrombin generation assays. However, other assays such as chromogenic assays applied for specific coagulation factors are also included. Examples of such assays or corresponding reagents are Pathromtin® SL (aPTT assay, Dade Behring) or Thromborel® S (Prothrombin time assay, Dade Behring) with corresponding coagulation factor deficient plasma (Dade Behring), Thrombin generation assay kits (Technoclone™, Thrombinoscope™) using e.g.

coagulation factor deficient plasma, chromogenic assays like Biophen™ Factor IX (Hyphen BioMed), Staclot® FVIIa-rTF (Roche Diagnostics GmbH), Coatest® Factor VIII:C/4 (Chromogenix), or others.

For purposes of this invention, an increase in any one of the above assays or an equivalent coagulation-related assay is considered to show an increase in molar specific activity. For example, a 25% increase refers to a 25% increase in any of the above or an equivalent assay.

To determine whether therapeutic fusion proteins fall within the scope of the present invention, the standard against which the molar specific activity of these proteins is compared is a construct in which the respective coagulation factor and the respective HLEP are linked by a non-cleavable linker having the amino acid sequence GGGGGGV (SEQ ID NO: 94).

In the case of FIX, aPTT assays are often used for determination of coagulation activity. Such a coagulation assay (aPTT assay) is described in example 5 in more detail. However, other coagulation-related assays or assay principles may be applied to determine molar specific activity for FIX.

Recombinant therapeutic polypeptide drugs are usually expensive and not all countries can afford costly therapies based on such drugs. Increasing the in vivo recovery of such drugs could make the use of these products cheaper and subsequently more patients would benefit from them. In the case of the fusion proteins of the present invention an increased in vivo recovery would also be a desirable advantage. "In vivo recovery" as used herein in the sense of the invention means the amount of product found in blood or plasma shortly after administration of the product. For detection of the in vivo recovery in general the plasma content is determined a few minutes (e.g. 5 or 15 min) after administration of the product.

Although it is desirable to have a high in vivo recovery and a long half-life for a non-activated coagulation factor, it is advantageous to limit the half-life of a coagulation factor after its activation or the activation of its co-factor in order to avoid a prothrombotic risk. Therefore, after the coagulation process has been initiated, the half-life of the active coagulation factor should again be reduced. This can either be achieved by enhancing inactivation in a coagulation-related mode or by elimination of the coagulation factor.

"Inactivation" according to the present invention means the decrease of activity of the therapeutic polypeptide which can be caused, for example, by a complex formation of a coagulation factor and an inhibitor of the corresponding coagulation factor or by further proteolytic cleavage as known, e.g., in the case of FVIII and FV.

The "inactivation rate" of an activated therapeutic fusion protein is defined as the rate the activity is declining, e.g., by reaction with inhibitors or by proteolytic inactivation. The inactivation rate may be measured by following the molar specific activity of the activated coagulation factor over time in the presence of physiologic amounts of inhibitors of this coagulation factor. Alternatively, the inactivation rate may be determined after administration of the activated product to an animal followed by testing of plasma samples at an appropriate time frame using activity and antigen assays.

To determine whether therapeutic fusion proteins fall within the scope of the present invention, the standard against which the molar specific activity of these proteins is compared is a construct in which the respective coagulation factor and the respective HELP are linked by a non-cleavable linker having the amino acid sequence GGGGGGV (SEQ ID NO: 94).

The "elimination rate" of an activated therapeutic fusion protein is defined as the rate the polypeptide is eliminated from the circulation of humans or other animals. The elimination rate may be determined by measuring the pharmacokinetics of the activated, therapeutic fusion protein after intravenous administration. Using an antigen assay, the elimination by direct removal from the circulation can be determined. Using an activity assay in addition, a specific removal and inactivation rate may be determined.

To determine whether therapeutic fusion proteins fall within the scope of the present invention, the standard against which the molar specific activity of these proteins is compared is a construct in which the respective coagulation factor and the respective HELP are linked by a non-cleavable linker having the amino acid sequence GGGGGGV (SEQ ID NO: 94).

According to some embodiments of this invention, the therapeutic polypeptide moiety is coupled to the HLEP moiety by a cleavable peptide linker. The linker should be non-immunogenic and should be flexible enough to allow cleavage by proteases. The cleavage of the linker should proceed comparably fast as the activation of the therapeutic polypeptide within the fusion protein, if the fusion protein is a zymogen.

The cleavable linker may comprise a sequence derived from a) the therapeutic polypeptide to be administered itself if it contains proteolytic cleavage sites that are proteolytically cleaved during activation of the therapeutic polypeptide, b) a substrate polypeptide of this therapeutic polypeptide, or c) a substrate polypeptide cleaved by a protease which is activated or formed by the direct or indirect involvement of the therapeutic polypeptide.

The peptide linker in some embodiments comprises a sequence of the therapeutic polypeptide to be applied, which should result in a decreased risk of neoantigenic properties of the expressed fusion protein. Also in case the therapeutic protein is a zymogen (e.g. needs to be proteolytically activated) the kinetics of the peptide linker cleavage will more closely reflect the coagulation-related activation kinetics of the zymogen in some embodiments.

In some embodiments, the therapeutic polypeptide is FIX zymogen and the HLEP is albumin. In some of those embodiments the linker sequence is either derived from the sequences of the activation regions of FIX, from the cleavage region of any substrate of FIX like FX or FVII or from the cleavage region of any substrate polypeptide that is cleaved by a protease in whose activation FIXa is involved.

In yet other embodiments, the linker peptide is derived from FIX itself. In other embodiments the linker peptide is derived from FX or FVII. In other embodiments the linker sequence comprises two cleavage sequences that can be cleaved by FXIa or FVIIa/TF, two physiologically relevant activators of FIX.

Exemplary combinations of therapeutic polypeptide, peptide linker, and HLEP include the constructs listed in tables 3a and 3b, but are not limited to them:

TABLE 3a

Examples of possible constructs

| Coagulation factor | Linker | HLEP | Linker derived from (with modifications, if applicable) | SEQ ID NO: |
|---|---|---|---|---|
| | Linker not cleavable or not sufficiently rapidly cleavable | | | |
| FIX | — | HSA | | |
| FIX | RI | HSA | | |
| FIX | GGGGGGV(Sheffield et al.) | HSA | | 94 |
| FIX | (GGS)nGS | HSA | | |
| FIX | SS(GGS)₇GS | HSA | | 30 |
| FIX | SSNGS(GGS)₃NGS(GGS)₃GGNGS | HSA | | 31 |
| | Linker with one cleavage site | | | |
| FIX (1-412) | SVSQTSKLTRAETVFPDVD | HSA | FIX | 36 |
| FIX (1-412) | SVSQTSKLTRAETVFPDVDGS | HSA | FIX | 37 |
| FIX | SVSQTSKLTRAETVFPDVD | HSA | FIX | 38 |
| FIX | SVSQTSKLTRAETVFPDVDGSGGS | HSA | FIX | 95 |
| FIX | SVSQTSKLTRAETVFPDVDGS | HSA | FIX | 39 |
| FIX | SVSQTSKLTRAETVFPDVDNGS | HSA | FIX | 40 |
| FIX | SVSQTSKLTRAETVFPDV | HSA | FIX | 96 |
| FIX | QTSKLTRAETVFPDV | HSA | FIX | 97 |
| FIX | SKLTRAETVFPDV | HSA | FIX | 98 |
| FIX | SVSQTSKLTRAETVFP | HSA | FIX | 99 |
| FIX | SVSQTSKLTRAETVF | HSA | FIX | 100 |
| FIX | QTSKLTRAETVF | HSA | FIX | 101 |
| FIX | SKLTRAETVF | HSA | FIX | 102 |
| FIX | SVSQTSKLTRAET | HSA | FIX | 103 |
| FIX | QTSKLTRAET | HSA | FIX | 104 |
| FIX | SKLTRAET | HSA | FIX | 105 |
| FIX | SVSQTSKLTRGETVFPDVD | HSA | FIX | 41 |
| FIX | SVSQTSKLTRTETVFPDVD | HSA | FIX | 42 |
| FIX | SVSQTSKLTRSETVFPDVD | HSA | FIX | 43 |
| FIX | SVSQTSKLTRLETVFPDVD | HSA | FIX | 44 |
| FIX | SVSQTSKLTRTEAVFPDVD | HSA | FIX | 45 |
| FIX | SVSQTSKLTRGEAVFPDVD | HSA | FIX | 46 |
| FIX | QTSKLTRAETVFPDVDGS | HSA | FIX | 106 |
| FIX | SKLTRAETVFPDVDGS | HSA | FIX | 107 |
| FIX | SKLTRAETVFPDVD | HSA | FIX | 47 |
| FIX | QSFNDFTRVVGGED | HSA | FIX | 48 |
| FIX | QSFNDFTRVVGGEDGS | HSA | FIX | 49 |

TABLE 3a-continued

Examples of possible constructs

| Coagulation factor | Linker | HLEP | Linker derived from (with modifications, if applicable) | SEQ ID NO: |
|---|---|---|---|---|
| FIX | QSFNDFTRVVGGE | HSA | FIX | 108 |
| FIX | QSFNDFTRTVGGED | HSA | FIX | 50 |
| FIX | QSFNDFTRLVGGED | HSA | FIX | 51 |
| FIX | QSFNDFTRGVGGED | HSA | FIX | 52 |
| FIX | QSFNDFTRVVSGEDNGS | HSA | FIX | 53 |
| FIX | QSFNDFTRVVGGEDN | HSA | FIX | 54 |
| FIX | PERGDNNLTRIVGGQEGS | HSA | FX | 109 |
| FIX | PERGDNNLTRIVGGQE | HSA | FX | 61 |
| FIX | PERGDNNLTRIVGGQ | HSA | FX | 110 |
| FIX | DNNLTRIVGGQ | HSA | FX | 111 |
| FIX | SVSQTSKLTRAETVFPDVD | Fc | FIX | 62 |
| FIX | QSFNDFTRVVGGEDN | Fc | FIX | 63 |
| FIX (1-412) | SVSQTSKLTRAETVFPDVD | Fc | FIX | 64 |
| FIX | ASKPQGRIVGG | HSA delDAH | FVII | 112 |
| FIX | KRNASKPQGRIVGGKV | HSA | FVII | 65 |
| FIX | PEEPQLRMKNNEEAED | HSA | FVIII | 66 |
| FIX | DNSPSFIQIRSVAKKHPKT | HSA | FVIII | 67 |
| FIX | LSKNNAIEPRSFSQNSRHPS | HSA | FVIII | 68 |
| FIX | DEDENQSPRSFQKKTRHYFIA | HSA | FVIII | 69 |
| FIX | SPHVLRNRAQSGSVPQ | HSA | FVIII | 70 |
| FVII or FVIIa | PEEPQLRMKNNEEAEDYDDDLTDS | HSA | FVIII | 71 |
| FVII or FVIIa | DDDNSPSFIQIRSVAKKHPKTWVHYAAEEED | HSA | FVIII | 72 |
| FVII or FVIIa | LSKNNAIEPRSFSQNSRHPSTRQKQFNA | HSA | FVIII | 73 |
| FVII or FVIIa | DEDENQSPRSFQKKTRHYFIAA | HSA | FVIII | 74 |
| FVII or FVIIa | DYGMSSSPHVLRNRAQSGSVPQFKKVVFQEFT | HSA | FVIII | 75 |
| FVIII | Derived from cleavage sites of FVIII, FIX, or Fibrinogen | HSA | FVIII, FIX or Fgn | |
| VWF | Derived from cleavage sites of VWF, FVIII, or FIX | HSA | FIX, FVIII, VWF | |
| VWF | DIYDEDENQSPRSFQKKTRHYFIA | HSA | FVIII | 76 |
| VWF | DNSPSFIQIRSVAKKHP | HSA | FVIII | 77 |
| VWF | LSKNNAIEPRSFSQNSRHPS | HSA | FVIII | 78 |
| FIX | PVSQTSKLTRAETVFPDV | HSA | FIX | 113 |
| FIX | PSVSQTSKLTRAETVFPDV | HSA | FIX | 114 |

In the case of linkers derived from the N-terminal region of the FIX activation peptide, according to the natural polymorphism T148-A148 the sequences may also contain A instead of T at this position.

| Coagulation factor | Linker | HLEP | Linker derived from (partially incl. Modifications) | SEQ ID NO: |
|---|---|---|---|---|
| | Linker with two cleavage sites | | | |
| FIX | SVSQTSKLTRAETVFPDVTQPERGDNNLTRIVGGQE | HSA | FIX, FX | 79 |
| FIX | SKLTRAETVFPDNNLTRIVGGQE | HSA | FIX, FX | 80 |
| FIX | RAETVFPDVTQPERGDNNLTRIVGGQE | HSA | FIX, FX | 81 |
| FIX | RAETVFPERGDNNLTRIVGGQE | HSA | FIX, FX | 82 |
| FIX | SVSQTSKLTRAETVFPDVDYVNNLTRIVGGQE | HSA | FIX, FX | 83 |
| FIX | SVSQTSKLTRAETVFPDVDNNLTRIVGGQE | HSA | FIX, FX | 84 |
| FIX | SVSQTSKLTRAETVFPDVDNNLTRIVGGQE | HSA | FIX, FX | 85 |
| FIX | SVSQTSKLTRAETVFPDVDYVNSTEAETILDNITQSTQSFNDFTRVVGGEDA | HSA | FIX | 86 |
| FIX | SVSQTSKLTRAETVFPDVQSFNDFTRVVGGED | HSA | FIX | 87 |
| FIX | SVSQTSKLTRAETVFPDVDSFNDFTRVVGGED | HSA | FIX | 88 |
| FIX | SVSQTSKLTRAETVFPDVNASKPQGRIVGGKV | HSA | FIX and FVII | 89 |
| FIX | SVSQTSKLTRAETVFPDVNASKPQGRLVGGKV | HSA | FIX and FVII | 90 |
| FIX | SVSQTSKLTRAETVFPDVNASKPQGRTVGGKV | HSA | FIX and FVII | 91 |
| FIX | SVSQTSKLTRAETVFPDVD | Fc | | 92 |

Variants and fragments of the linkers described in tables 3a and 3b are also encompassed in the present invention as long as the linkers can still be cleaved by the protease or the proteases that cleave the linkers of tables 3a and 3b or by the type of proteases defined above.

Other combinations of the cleavage sequences described above and their variants shall be included in the present invention.

In another embodiment, amino acid substitutions are included that change the post-translational modification pattern of the peptide linker. These can be, for example, substitutions of amino acids that are glycosylated, sulphated, or phosphorylated.

In another embodiment of the invention the peptide linker between the therapeutic polypeptide and the HLEP moiety contains consensus sites for the addition of posttranslational modifications. Such modifications may comprise glycosylation sites. For example, such modifications may comprise at least one N-glycosylation site of the structure Asn-X-Ser/Thr, wherein X denotes any amino acid except proline. Furthermore, such N-glycosylation sites may be inserted close to the amino and/or carboxy terminus of the peptide linker such that they are capable of shielding potential neo-epitopes which might develop at the sequences where the therapeutic polypeptide moiety is transitioning into the peptide linker or where the peptide linker is transitioning into, for example, an albumin moiety sequence.

about 1:500. One fusion protein with non-cleavable linker (1478/797) and two fusion proteins with cleavable linker (1088/797 and 1089/797) were used. Samples were analyzed by SDS-PAGE under reducing conditions followed by Coomassie blue staining FIG. 2: Pharmacokinetics of activated rec FIX and FIX-albumin fusion proteins with and without cleavable linker in comparison to non-activated fusion proteins.

Figure 3:
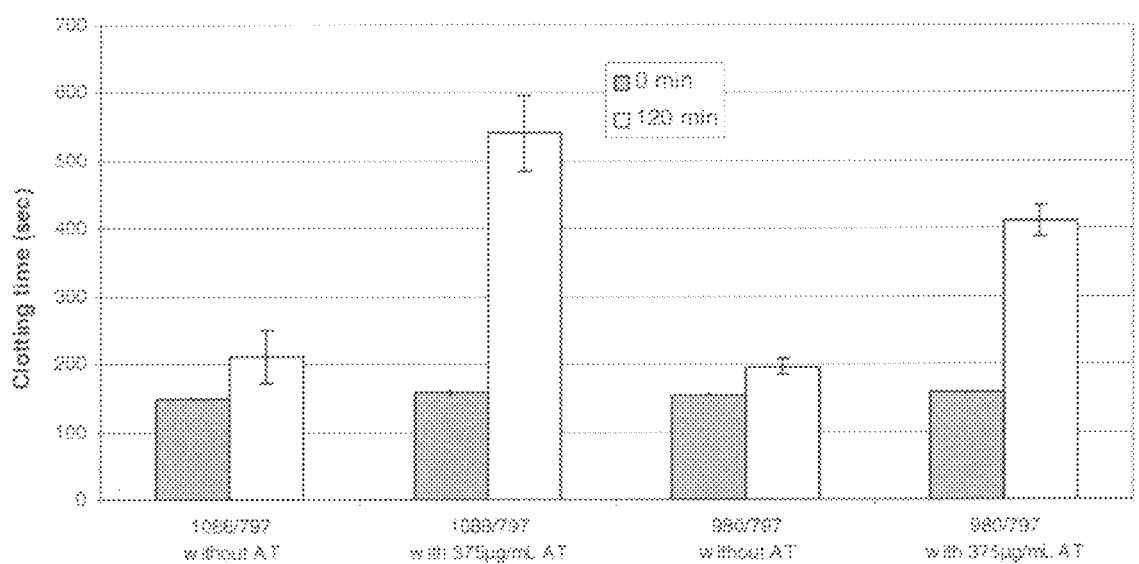

FIG. 3: Inactivation of activated rec FIX or FIX-albumin fusion protein by AT. Residual FIX activity was determined after 120 min using a non-activated partial thromboplastin time assay.

EXAMPLES

Example 1

Generation of cDNAs Encoding FIX and FIX-Albumin Fusion Proteins

Factor IX coding sequence was amplified by PCR from a human liver cDNA library (ProQuest, Invitrogen) using primers We1403 and We1404 (SEQ ID NOS:5 and 6). After a second round of PCR using primers We1405 and We1406 (SEQ ID NOS:7 and 8) the resulting fragment was cloned into pCR4TOPO (Invitrogen). From there the FIX cDNA was transferred as an EcoRI Fragment into the EcoRI site of pIRESpuro3 (BD Biosciences) wherein an internal XhoI site had been deleted previously. The resulting plasmid was designated pFIX-496 and was the expression vector for factor IX wild-type.

For the generation of albumin fusion constructs the FIX cDNA was reamplified by PCR under standard conditions using primers We2610 and We2611 (SEQ ID NOS:9 and 10) deleting the stop codon and introducing an XhoI site instead. The resulting FIX fragment was digested with restriction endonucleases EcoRI and XhoI and ligated into an EcoRI/BamH1 digested pIRESpuro3 together with one XhoI/BamH1 digested linker fragment as described below.

Two different glycine/serine linker fragments without internal cleavage sites were generated: Oligonucleotides We2148 and We2150 (SEQ ID NOS:11 and 12) were annealed in equimolar concentrations (10 pmol) under standard PCR conditions, filled up and amplified using a PCR protocol of a 2 min. initial denaturation at 94° C. followed by 7 cycles of 15 sec. of denaturation at 94° C., 15 sec. of annealing at 55° C. and 15 sec. of elongation at 72° C., and finalized by an extension step of 5 min at 72° C. The same procedure was performed using oligonucleotides We2156 and We2157 (SEQ ID NOS:13 and 14). The resulting linker fragments were digested with restriction endonucleases XhoI and BamH1 and used separately in the above described ligation reaction. The resulting plasmids therefore contained the coding sequence for FIX and a C-terminal extension of a glycine/serine linker.

Two different cleavable linker fragments derived from the activation sites of FIX were generated: Oligonucleotides We2335 and We2336 (SEQ ID NOS:15 and 16), containing the activation cleavage site of the FIX light chain/activation peptide border region, were annealed, filled, and amplified as described above. The resulting linker fragment was digested with restriction endonucleases XhoI and BamH1 and used in the above described ligation reaction. The resulting plasmid therefore contained the coding sequence for FIX and a C-terminal extension of a cleavable FIX sequence (amino acids 136 to 154 of SEQ ID NO:2). In a subsequent site directed mutagenesis reaction with a commercially available mutagenesis kit (QuickChange XL Site Directed Mutagenesis Kit, Stratagene) using oligonucleotides We2636 and We2637 (SEQ ID NOS:17 and 18) the XhoI site was deleted.

For generation of the second cleavable linker fragment derived from FIX, the same procedure was performed using oligonucleotides We2337 and We2338 (SEQ ID NOS:19 and 20) for linker construction. The resulting linker fragment was digested with restriction endonucleases XhoI and BamH1 and used in the above described ligation reaction. The resulting plasmid now contained the coding sequence for FIX and a C-terminal extension of a cleavable FIX sequence derived from the activation cleavage site of the FIX activation peptide/heavy chain border region (amino acids 173 to 186 of SEQ ID NO:2). Oligonucleotides We2638 and We 2639 (SEQ ID NOS:21 and 22) were used for deletion of the XhoI site as described above.

In the next cloning step the above generated plasmids were digested with BamH1 and a BamH1 fragment containing the cDNA of mature human albumin was inserted. This fragment had been generated by PCR on an albumin cDNA sequence using primers We1862 and We1902 (SEQ ID NOS:23 and 24) under standard conditions.

The final plasmids with non-cleavable glycine/serine linkers were designated pFIX-980 (SEQ ID NO:30) and pFIX-986 (SEQ ID NO:31), respectively. The final plasmids with cleavable linkers derived from FIX sequences were designated pFIX-1088 (SEQ ID NO:40) and pFIX-1089 (SEQ ID NO:49), respectively. Their linker sequences and the C-terminal FIX and N-terminal albumin sequences are outlined below. Proteolytic cleavage sites within the linkers are indicated with arrows, the FIX derived linker sequences are underlined.

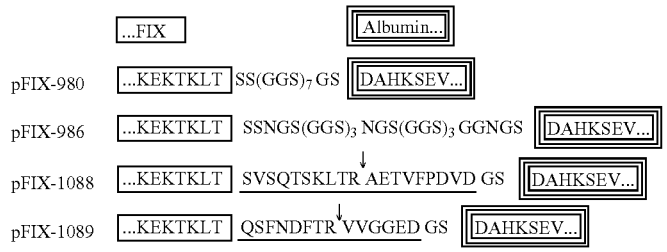

For expression in CHO cells the coding sequences for the FIX albumin fusion protein were transferred into vectors pIRESneo3 (BD Biosciences) or pcDNA3.1 (Invitrogen), respectively.

Using the above protocols and plasmids and by applying molecular biology techniques known to those skilled in the art (and as described e.g. in Current Protocols in Molecular Biology, Ausubel FM et al. (eds.), including Supplement 80, published October 2007, John Wiley & Sons, Inc.) other constructs can be made with insertions of different linker sequences, e.g. as described in tables 3a and 3b.

For efficient processing of the propeptide in cells expressing FIX in high amounts coexpression of furin is required (Wasley L C et al. 1993. PACE/Furin can process the vitamin K-dependent pro-factor IX precursor within the secretory pathway. J. Biol. Chem. 268:8458-8465). Furin was amplified from a liver cDNA library (Ambion) using primers We1791 and We1792 (SEQ ID NOS:25 and 26). A second round of PCR using primers We1808 and We1809 (SEQ ID NOS:27 and 28) yielded a furin fragment where the carboxy-terminal transmembrane domain (TM) was deleted and a stop codon introduced; this fragment was cloned into pCR4TOPO (Invitrogen). From there the furinΔTM cDNA was transferred as an EcoRI/NotI Fragment into the EcoRI/NotI sites of pIRESpuro3 (BD Biosciences) wherein an internal XhoI site had been deleted previously. The resulting plasmid was designated pFu-797. This plasmid was cotransfected with all FIX constructs in a 1:5 (pFu-797: pFIX-xxx) molar ratio. The amino acid sequence of the secreted furin encoded by pFu-797 is given as SEQ-ID NO:29.

Example 2

Transfection and Expression of FIX and FIX-Albumin Fusion Proteins

Plasmids were grown up in *E. coli* TOP10 (Invitrogen) and purified using standard protocols (Qiagen). HEK-293 cells were transfected using the Lipofectamine 2000 reagent (Invitrogen) and grown up in serum-free medium (Invitrogen 293 Express) in the presence of 50 ng/ml Vitamin K and 4 µg/ml Puromycin. Transfected cell populations were spread through T-flasks into roller bottles or small-scale fermenters from which supernatants were harvested for purification.

Alternatively, CHO K1 or DG44 cells (Invitrogen) were transfected using the Lipofectamine 2000 reagent (Invitrogen) and grown up in serum-free medium (Invitrogen CD-CHO) in the presence of 50 ng/ml Vitamin K and 500-750 ng/ml Geneticin. High expressing clones were selected and spread through T-flasks into roller bottles or small-scale fermenters from which supernatants were harvested for purification.

Example 3

Purification of FIX and FIX-Albumin Fusion Proteins

Cell culture harvest containing FIX or FIX albumin fusion protein was applied on a Q-Sepharose FF column previously equilibrated with 50 mM TrisxHCl/100 mM NaCl buffer pH 8.0. Subsequently, the column was washed with equilibration buffer containing 200 mM NaCl. Elution of the bound FIX or FIX fusion protein was achieved by a salt gradient using 50 mM TrisxHCl/200 mM NaCl buffer pH 8.0 as a basis. The eluate was further purified by column chromatography on a hydroxylapatite resin. For this purpose, the eluate of the Q-Sepharose FF column was loaded on a hydroxylapatite chromatography column equilibrated with 50 mM TrisxHCl/100 mM NaCl buffer pH 7.2. The column was washed with the same buffer and FIX or FIX-HSA were eluted using a potassium phosphate gradient at pH 7.2. The eluate was dialyzed to reduce the salt concentration and used for biochemical analysis as well as for determination of the pharmacokinetic parameters. FIX antigen and activity were determined as described in example 5.

Example 4

Alternative Purification Scheme of FIX and FIX-Albumin Fusion Proteins

As described in example 3, cell culture harvest containing FIX or FIX albumin fusion protein was purified by chromatography on Q-Sepharose FF. The Q-Sepharose eluate was further purified by chromatography on a Heparin-Fractogel column. For this purpose, the Heparin-Fractogel column was equilibrated using 50 mM TrisxHCl, 50 mM NaCl pH 8.0 buffer (EP), the Q-Sepharose FF eluate was applied and the column was washed with equilibration buffer containing 75 mM NaCl. FIX or FIX albumin fusion protein, respectively, was eluted using EP adjusted to 300 mM NaCl.

The Heparin-Fractogel eluate was further purified by chromatography on a hydroxylapatite chromatography column as described in example 3. The purified FIX resp. FIX albumin fusion protein concentrate was subjected to FIX activity and antigen determination according to example 5 and characterized by further in vitro and in vivo investigations.

Example 5

Determination of FIX Activity and Antigen

FIX activity was determined as clotting or coagulation activity (FIX:C) using commercially available aPTT reagents (Pathromtin SL and FIX depleted plasma, Dade Behring). An internal substandard calibrated against the WHO International FIX concentrate Standard (96/854) was used as a reference.

FIX antigen (FIX:Ag) was determined by an ELISA acc. to standard protocols known to those skilled in the art. Briefly, microtiter plates were incubated with 100 µL per well of the capture antibody (Paired antibodies for FIX ELISA 1:200, Cedarlane, but other sources of appropriate antibodies may also be applied) overnight at ambient temperature. After washing plates three times with washing buffer B (Sigma P3563), each well was incubated with 200 µL blocking buffer C (Sigma P3688) for one hour at ambient temperature. After another three wash steps with buffer B, serial dilutions of the test sample in buffer B as well as serial dilutions of a substandard (SHP) in buffer B (volumes per well: 100 µL) were incubated for two hours at ambient temperature. After three wash steps with buffer B, 100 µL of a 1:200 dilution of the detection antibody (Paired antibodies for FIX ELISA, peroxidase labelled, Cedarlane) in buffer B were added to each well and incubated for another two hours at ambient temperature. After three wash steps with buffer B, 100 µL of substrate solution (TMB, Dade Behring, OUVF) were added per well and incubated for 30 minutes at ambient temperature in the dark. Addition of 100 µL undiluted stop solution (Dade Behring, OSFA) prepared the samples for reading in a suitable microplate reader at 450 nm wavelength. Concentrations of test samples were then calculated using the standard curve with standard human plasma as reference.

Example 6

Comparison of FIX-Activity/FIX-Antigen Ratio of Different FIX-Albumin Fusion Proteins in Cell Culture Supernatant Cell culture supernatants of HEK cells transfected with DNA constructs coding for FIX-albumin fusion proteins that contained different linker peptides were subjected to FIX activity and antigen testing as described above (see example 5). The ratio of FIX:C to FIX:Ag was calculated representing a measure directly proportional to molar specific activity of the different constructs.

The results shown in table 4 indicate that there is an increase in activity/antigen ratio upon introduction of cleavable linkers into the FIX-HSA molecule. It also shows that the cleavable linker peptide should have a length of more than two amino acids in order to provide clearly increased activity/antigen ratios.

TABLE 4

FIX:C/FIX:Ag ratios of FIX-albumin fusion proteins containing different linker peptides

| FIX-HSA construct | Linker | FIX:C/ FIX:Ag | Fold increase compared to fusion protein 980/797 with non-cleavable linker (GGGGGGV) |
|---|---|---|---|
| 1182/797 | None | <0.031 | |
| 1366/797 | RI | <0.068 | |
| 1478/863 | GGGGGGV (Sheffield et al.) (SEQ ID NO: 94) | 0.041 | — |
| 980/797 | SS(GGS)₇GS (SEQ ID NO: 30) | 0.070 | 1.7 |
| 986/797 | SSNGS(GGS)3NGS (GGS)3GGNGS (SEQ ID NO: 31) | 0.076 | 1.9 |
| 1483/863 | SVSQTSKLTRAETVFPDVD GSGGS (SEQ ID NO: 95) | 0.688 | 16.8 |
| 1088/797 | SVSQTSKLTRAETVFPDVDGS (SEQ ID NO: 39) | 0.832 | 20.3 |
| 1365/797 | SVSQTSKLTRAETVFPDVD (SEQ ID NO: 36) | 0.630 | 15.4 |
| 1482/863 | SVSQTSKLTRAETVFP (SEQ ID NO: 99) | 0.482 | 11.8 |
| 1087/797 | SVSQTSKLTRAETVFPDVDGS (FIX deltaKLT) (SEQ ID NO: 39) | 0.472 | 11.5 |
| 1089/797 | QSFNDFTRVVGGEDGS (SEQ ID NO: 49) | 0.532 | 13.0 |
| 1091/797 | PERGDNNLTRIVGGQEGS (SEQ ID NO: 109) | 0.111 | 2.7 |

Example 7

Comparison of FIX and FIX-Albumin Fusion Proteins in Respect to Molar Specific Activity, Terminal In Vivo Half-Life and In Vivo Recovery in Rats or Rabbits Purified recombinant wild type FIX (rFIX 496/797) and FIX-albumin fusion proteins (rFIX 980/797, rFIX 986/797, rFIX-1088/797 and rFIX 1089/797) were tested for FIX activity in a clotting assay as described above. In parallel, the difference of the optical density at 280 and 320 nm was determined as a measure for protein concentration (OD280-320). The ratios of activity per OD280-320 were calculated and based on the molar optical densities the molar specific activities were calculated. In the following table 5 the results are summarized.

TABLE 5

Molar specific activities of wt FIX compared to FIX-albumin fusions (linker sequence correspond to SEQ ID NOS 94, 30 & 31, respectively, in order of appearance)

| | Linker | Optical density (OD280-320) | FIX clotting activity (IU/mL) | Activity/ Vol/OD (IU/mL/OD) | Molar specific activity* (IU/nmol) |
|---|---|---|---|---|---|
| rFIX, wt (496/797) | — | 0.3798 | 21.2 | 55.8 | 4.23 |
| rFIX-HSA (non-cleavable, 1478/863) | GGGGGGV (Sheffield et al.) | 2.9189 | 5.8 | 2.0 | 0.23 |
| rFIX-HSA (non-cleavable, 980/797) | SS(GGS)₇GS | 1.1122 | 3.4 | 3.0 | 0.35 |
| rFIX-HSA (non-cleavable, 986/797) | SSNGS(GGS)3NGS(GGS)3GGNGS | 0.8107 | 3.2 | 4.0 | 0.45 |
| rFIX-HSA (cleavable, 1088/797) | FXIa cleavable | 0.3421 | 11.9 | 34.8 | 3.95 |
| rFIX-HSA (cleavable, 1089/797) | FXIa cleavable | 0.4512 | 11.3 | 25.0 | 2.84 |

*Molar specific activity based on activity, optical density and the following molar optical densities:
Molar optical density of FIX: OD(280 nm, 1 mol/L) = 75 810
Molar optical density of albumin: OD(280 nm, 1 mol/L) = 37 791
Molar optical density of FIX-albumin fusion protein: OD(280 nm, 1 mol/L) = 113 601

Taking the results summarized in Table 5 into account, two constructs that were generated according to the present invention show highly increased molar specific activities compared to the fusion proteins with non-cleavable linkers. In addition, the molar specific activity of these constructs was only moderately decreased compared to wild type rFIX.

Figure 1:
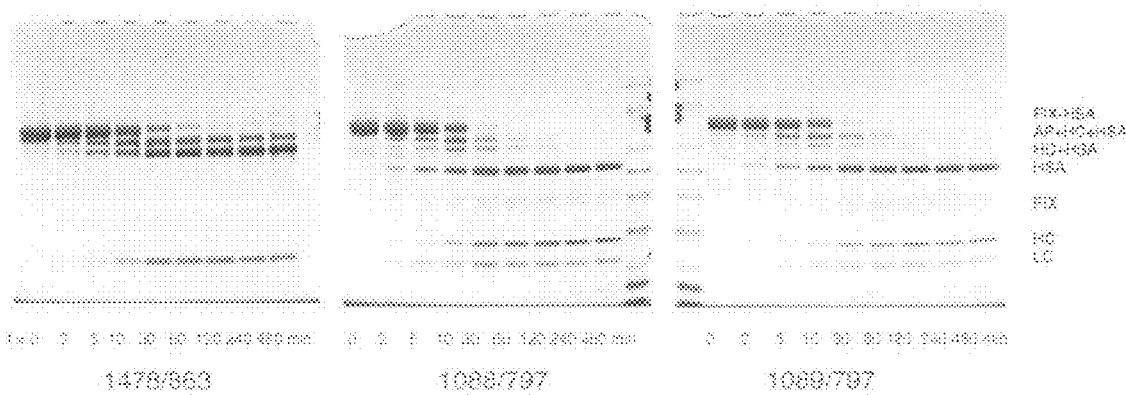
FIG. 1: In vitro activation of FIX-albumin fusion proteins by FXIa at 37° C. at a molar ratio of FXIa to fusion protein of TABLE 3b Examples of possible constructs with two or more cleavage sites

In vitro investigations of the proteolytic cleavage reactions by Factor XIa (FXIa) confirmed that FIX-albumin fusion proteins containing a cleavable linker such as construct no. 1088/797 or 1089/797 are activated and in parallel the linker is cleaved resulting in release of the albumin moiety (FIG. 1).

The fusion protein with non-cleavable linker did not show a corresponding release of the albumin moiety.

In the case of FVIIa as cleaving protease in the presence of tissue factor, the FIX-albumin fusion proteins 1088/797 or 1089/797 containing a cleavable linker also showed release of the albumin moiety in parallel to release of the FIX activation peptide (Data not shown).

In addition to determination of molar specific coagulation activity, the polypeptides no. 496/797, 980/797, 986/797, 1088/797 and 1089/797 described above were administered intravenously to narcotized CD/Lewis rats (6 rats per substance) and/or rabbits (4 rabbits per substance) with a dose of 50 IU/kg body weight. Blood samples were drawn prior to test substance administration and at appropriate intervals starting at 5 minutes after administration of the test substances. FIX antigen content was subsequently quantified by an ELISA assay specific for human Factor IX (see above). The mean values of the respective groups were used to calculate in vivo recovery after 5 min. Half-lives for each protein were calculated using the time points of the beta phase of elimination (terminal half-life) according to the formula $t_{1/2}=\ln 2/k$, whereas k is the slope of the regression line obtained upon plotting FIX:Ag levels in logarithmic scale and time in linear scale.

Calculated in vivo half-lives are summarized in table 6. In rats as well as in rabbits the in vivo half-lives of the FIX-albumin fusion proteins were found to be significantly increased in comparison to non-fused wild-type recombinant FIX prepared in-house or in comparison to the commercially available recombinant FIX product BeneFIX®. The in vivo half-lives of the albumin fusion proteins compared to BeneFIX® were increased to about 200-400%, depending on the animal species or construct used (Table 6).

To evaluate the in vivo recovery, the FIX antigen levels measured per mL of plasma at their maximum concentrations after intravenous administration (t=5 min) were related to the amount of product applied per kg. Alternatively, a percentage was calculated by relating the determined antigen level (IU/mL) 5 min post infusion to the theoretical product level expected at 100% recovery (product applied per kg divided by an assumed plasma volume of 40 mL per kg). The in vivo recoveries (IVR) of the FIX-albumin fusion proteins were significantly higher than the in vitro recoveries of rFIX (496/797) or BeneFIX® (Table 7).

TABLE 6

Terminal in vivo half-lives of FIX preparations derived from recombinant expression (BeneFIX ®, rFIX 496/797) and FIX albumin fusion proteins (rFIX 980/797, rFIX 986/797, rFIX 1088/797, and rFIX 1089/797) after intravenous administration of 50 IU/kg into rats and/or 50 IU/kg into rabbits, respectively.

|  | Rat experiments PSR18-05, PSR06-05, PSR02-05 | | Rabbit experiment PSK11-05 | |
|---|---|---|---|---|
|  | Terminal half-life (h) | relative to BeneFIX [%] | Terminal half-life (h) | relative to BeneFIX [%] |
| rFIX 496/797 | 4.5* | 91 | n.t. | n.t. |
| rFIX 980/797 | 11.6* | 234 | 36.9° | 410 |
|  |  |  | 29.3° ($2^{nd}$ exp.) | 326 |
| rFIX 986/797 | 10.5* | 212 | n.t. | n.t. |
| rFIX 1088/797 | 8.3* | 168 | 30.3° | 337 |
| rFIX 1089/797 | 10.5* | 212 | n.t. | n.t. |
| BeneFIX | 4.95* (mean of 5.3 and 4.6) | 100 | 9.0° | 100 |

*Determined between 120 and 1440 min
°Determined between 4 and 96 h

TABLE 7

In vivo recoveries (amount of substance 5 minutes post administration) of recombinant FIX preparations (BeneFIX, rFIX 496/797) and FIX albumin fusion proteins (rFIX 1088/797, rFIX 1089/797) after intravenous administration of 50 IU/kg into rats. The percentage of in vivo recovery was calculated based on an assumed plasma volume of 40 mL/kg.

|  | rat experiment | |
|---|---|---|
|  | in vivo recovery IU/dL per IU/kg/[%]* | relative to BeneFIX [%] |
| rFIX 496/797 | 0.462/18.5 | 74.6 |
| rFIX 1088/797 | 1.034/41.4 | 166.5 |
| rFIX 1089/797 | 1.063/42.5 | 171.2 |
| BeneFIX | 0.621/24.8 | 100 |

*Calculated based on a plasma volume of 40 mL/kg

Example 8

In Vitro Activation of FIX Albumin Fusion Proteins with/without Cleavable Linker (1088/797 and 980/797) and Determination of Pharmacokinetics in Rats FIX-albumin fusion proteins and rec FIX were activated in vitro using commercially available Factor XIa (Kordia). Briefly, identical molar amounts of FIX or FIX-albumin fusion protein ($3.0 \times 10^{-6}$ mol/L) were activated at 37° C. in solution in the presence of FXIa ($1.9 \times 10^{-8}$ mol/L) and $CaCl_2$ (1.5 mmol/L) buffered at pH 6.8. After complete activation as shown by SDS-PAGE the reaction was stopped by addition of a 5× molar excess of C1-Inhibitor (Berinert® P) based on the amount of FXIa. The samples were stored frozen below −70° C. until start of pharmacokinetic investigation.

Figure 2:
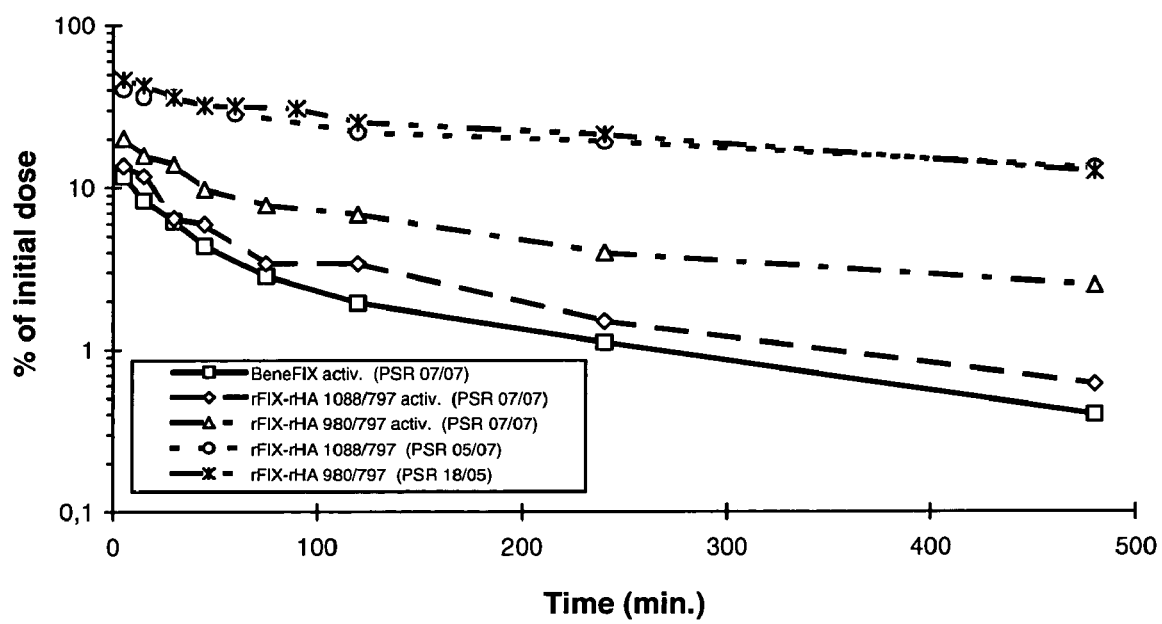

A pharmacokinetic investigation of the activated FIX and the FIX-albumin fusion proteins was performed in rats as described in example 7 and the results were compared to a pharmacokinetic results covering non-activated fusion proteins. It turned out that the activated fusion proteins demonstrated significantly reduced half-lives as well as AUC's compared to the non-activated molecules (FIG. 2). Upon activation the FIX-fusion protein with cleavable linker (1088/797) showed a pharmacokinetic behaviour very similar to activated rec FIX (BeneFIX®) whereas the activated fusion protein with non-cleavable linker (980/797) resulted in a higher initial as well as terminal half-life compared to activated fusion protein 1088/797 with cleavable linker. Therefore, in this example, the cleavable linker results in increased elimination of the coagulation factor after activation and, therefore, avoids accumulation of potentially thrombogenic, activated fusion proteins with extended half-lives.

Example 9

Comparison of FIX-Albumin Fusion Proteins with/without Cleavable Linker in Respect to Inactivation Rate of the Activated Coagulation Factors by Antithrombin III (AT)

FIX fusion proteins with (1088/797) and without (980/797) cleavable linker were activated by incubation with FXIa as described in example 8. The activated factors were incubated with AT for 120 min and residual FIXa activity was determined using a manual FIX clotting assay method without activation (naPTT, see below) acc. to Schnitger and Gross. As control samples the activated FIX-albumin fusion proteins were used in presence of the same amount of AT but without incubation.

The FIX activity was determined with the aid of a non-activated partial thromboplastin time assay (naPTT) using FIX deficient plasma from Dade Behring. The samples were prediluted in a buffer of pH 6.8 containing His, Gly, Sucrose, and Tween® 80. The whole determination was performed using coagulometers acc. to Schnitger & Gross. A mixture of 0.1 ml F IX deficient plasma, 0.1 ml sample, and 0.1 ml of 0.1% Phospholipids (Rhone-Poulenc-Nattermann, 1:3 prediluted in imidazole buffer supplemented with 1% HSA) was incubated for 2 minutes at 37° C. The coagulation reaction was initiated by adding 0.1 ml 0.025 mol/l $CaCl_2$ solution and the clotting time was determined.

FIG. 3 shows the results of a corresponding inactivation experiment. In the case of the fusion protein with cleavable linker (1088/797) an increase in clotting time from 210 to 540 sec (factor of 2.57×) demonstrated an accelerated inactivation process of FIXa activity by AT compared to a fusion protein with non-cleavable linker (980/797) that only showed an increase from 196 to 411 sec (factor of 2.10 x). Most probably, the albumin residue sterically affects the AT dependent inactivation process in the case of the fusion protein with non-cleavable linker whereas in the case of the fusion protein with cleavable linker the albumin residue is cleaved off resulting in an accelerated inactivation by AT.

Example 10

Design of FIX-HSA Fusion Proteins with Reduced Immunogenicity

As there is with any fusion between two proteins a slight risk associated that a neoepitope is created around the fusion point it was investigated whether the linker region as described in table 3a and 3b could be modified in order to decrease this risk.

In the course of this investigation all proposed linker sequences and the adjacent regions of FIX and HSA were analyzed for potential T-cell epitopes by way of prediction of binding capability to multiple MHC-II alleles. One of these approaches involved the PreDeFT analysis offered by the company EpiVax (146 Clifford St., Providence, R.I. 02903, USA) in which the input sequences were parsed into overlapping 9-mer frames where each frame overlaps the last by 8 amino acids. Each frame was then assessed for its ability to bind with a set of common HLA. These detailed findings were then summarized producing regional and overall assessments of immunogenic potential. Finally, any epitope clusters identified were screened against the non-redundant protein database at GenBank and EpiVax's own database of known MHC ligands and T-cell epitopes.

As a result of these in silico predictions the following FIX fusion proteins were cloned, expressed and purified

```
FIX- PVSQTSKLTRAETVFPDV-HSA      SEQ ID NO: 113

FIX-PSVSQTSKLTRAETVFPDV-HSA      SEQ ID NO: 114
```

Example 11

Neoantigenicity Test

FIX-HSA fusion proteins comprising linkers SEQ ID NO:113 or 114 can be shown to display a reduced immunogenicity compared to fusion proteins comprising different linkers or to display a comparable immunogenicity as compared to wild type factor FIX by the following neoantigenicity test.

Products to be compared are administered subcutaneously into rabbits with or in the absence of Freund's adjuvant. The endpoint assay is a native Western blot.

A suitable dose of either the FIX-HSA fusion with a linker with reduced immunogenicity or a FIX-HSA fusion with a linker of enhanced immunogenicity or FIX wild type can be administered as a slow bolus.

A sample can be taken about 30 to 40 days after the start of the immunization and be assayed by a Western blot method to ensure that the rabbits developed antibodies against each of the respective immunogens.

Antibodies against the test sample for which a potentially increased immunogenicity is to be measured are blocked by an excess of a control sample (e.g. wild type FIX) By doing so all of the antibodies present which formed against native epitopes are unable to react when that antibody is used as a probe in a Western blot. The test and the control sample are run on the Western blot membrane and the blocked antibody is used as a probe.

If there were epitopes on the test samples (here FIX-HSA fusion protein with a linker) but not in the control sample (wild type FIX) that caused antibody formation in the rabbits, these antibodies would be detected after blocking as residual antibodies which would react with the test sample, but not the control sample.

Likewise FIX-HSA with a linker having predicted reduced immunogenicity can be used as a control versus a FIX-HSA with a linker having predicted increased immunogenicity as a test sample.

Preferably the same Western blot is assayed with non-blocked antibodies raised against the test sample as a positive control. Here it is expected that test sample as well as control sample are detected in the Western blot assay.

If with blocked antibodies raised against the test sample both test and control sample are not detected it can be concluded that the test sample has no neoepitopes as compared to the control sample.

If with blocked antibodies raised against the test sample only the test sample but not the control sample is detected it can be concluded that the test sample has neoepitopes as compared to the control sample.

For doing the analysis the IgG fraction of the hyper immune pooled serum can be purified using a protein A column from Pierce or other suppliers with a bed volume for example greater than 1 ml according to the instructions of the supplier. Preferably the rabbit sera are dilapidated for example with trichlorotrifluoroethane.

Blocking is done for example by mixing 0.1-1.00 mg of the purified antiserum with 0.1 to 100 mg of the control sample in for example a 0.5 to 5 ml centrifuge cup, bringing the volume up to 0.5 to 3 ml. The tubes are then rotated slowly at room temperature of a minimum of 2 hours.

Nonblocked control antibodies to be used as a positive control can be prepared in the same way except that no control sample is used for blocking.

All blocked and nonblocked antibodies can be added to 3 to 4.5 ml of 5% dry milk solution in TBS+0.1% Tween-20 before incubation with their respective membrane.

Preferably Western blots are performed as native Western blots.

We claim:

1. A fusion protein comprising:
   a) a coagulation factor,
   b) a half-life enhancing polypeptide (HLEP) wherein the half-life enhancing polypeptide is, and
   c) a peptide linker which joins the coagulation factor and the half-life enhancing polypeptide;
   wherein the peptide linker is cleavable by proteases involved in coagulation, and wherein the fusion protein has, in comparison to a respective fusion protein linked by a non-cleavable linker having the amino acid sequence GGGGGGV (SEQ ID NO: 94), at least one of the following properties:
   i) an increased molar specific activity in at least one coagulation-related assay,
   ii) an increased inactivation rate of the activated coagulation factor after the peptide linker is proteolytically cleaved in a coagulation-related mode, and
   iii) an increased elimination rate of the activated coagulation factor after the peptide linker is proteolytically cleaved in a coagulation-related mode.

2. The fusion protein of claim 1, wherein said fusion protein has a higher in vivo recovery compared to the in vivo recovery of the coagulation factor when it is not fused to a half-life enhancing polylpeptide.

3. The fusion protein of claim 1, wherein said fusion protein has an increased half-life in plasma compared to the half-life in plasma of the coagulation factor when it is not fused to a half-life enhancing polylpeptide.

4. The fusion protein of claim 1 wherein the coagulation factor is a vitamin-K dependent coagulation factor.

5. The fusion protein according of claim 1 wherein the coagulation factor is FIX.

6. The fusion protein of claim 1 wherein the peptide linker is cleavable by FXIa and/or FVIIa/TF.

7. The fusion protein of claim 1, wherein the molar specific activity of the fusion protein is increased at least 25% compared to that of the respective fusion protein linked by a non-cleavable linker having the amino acid sequence GGGGGGV (SEQ ID NO: 94) in at least one coagulation-related assay.

8. The fusion protein of claim 1, wherein the inactivation rate of the coagulation factor after cleavage of the peptide linker which links the coagulation factor to the half-life enhancing polypeptide is increased by at least 10% as compared to the inactivation rate of the coagulation factor in the corresponding fusion protein linked by a non-cleavable linker having the amino acid sequence GGGGGGV (SEQ ID NO: 94).

9. The fusion protein of claim 1, wherein the elimination rate of the coagulation factor after cleavage of the peptide linker which links the coagulation factor to the half-life enhancing polypeptide is increased by at least 10% as compared to the elimination rate of the coagulation factor in the corresponding fusion protein linked by a non-cleavable linker having the amino acid sequence GGGGGGV (SEQ ID NO: 94).

10. The fusion protein of claim 1, wherein the linker is cleavable by a protease that naturally activates the coagulation factor in vivo.

11. The fusion protein of claim 10, wherein the kinetics of the linker cleavage by the protease is not delayed by more than a factor of 3 compared to the kinetics of the activation of said coagulation factor.

12. The fusion protein of claim 1, wherein the linker is cleavable by a protease that is naturally activated in vivo by the coagulation factor.

13. The fusion protein of claim 1, wherein the linker is cleavable by FXIa and/or by FVIIaTF, and wherein the coagulation factor is FIX.

14. The fusion protein of claim 1 wherein the linker is cleavable by FXa and/or FVIIa/TF, and wherein the coagulation factor is FVIIa.

15. The fusion protein of claim 1, wherein the linker comprises SEQ ID NO:113.

16. A polynucleotide encoding the fusion protein of claim 1.

17. A plasmid or vector comprising the polynucleotide of claim 16.

18. A plasmid or vector according to claim 17, which is an expression vector.

19. A plasmid or vector according to claim 17, wherein the vector is a transfer vector for use in human gene therapy.

20. A host cell comprising a polynucleotide according to claim 16.

21. A method of producing a fusion protein of claim 1, comprising culturing host cells comprising a polynucleotide encoding the fusion protein under conditions such that the fusion protein is expressed.

22. A pharmaceutical composition comprising
    (a) the fusion protein of claim 1,
    (b) a polynucleotide encoding said fusion protein, or
    (c) a plasmid or vector comprising a polynucleotide encoding said fusion protein.

23. A method of administering an effective amount of the fusion protein of claim 1 to a patient in need thereof, comprising
    (a) administering said fusion protein.

24. The method of claim 23, wherein the patient suffers from a blood coagulation disorder.

25. The method of claim 24, wherein the blood coagulation disorder is hemophilia B.

26. The method of claim 24, wherein the blood coagulation disorder is FVII and/or FVIIa deficiency.

27. The method according to claim 24, wherein the blood coagulation disorder is hemophilia A.

28. The method according to claim 24, wherein the fusion protein is effective to act in the patient as a procoagulant.

29. The fusion protein of claim 1, wherein the coagulation factor, albumin, or immunoglobulin comprises a sequence that is 95% identical to the sequence of a wild-type human coagulation factor, human serum albumin, or a wild-type human immunoglobulin.

30. The method of claim 21 further comprising recovering the fusion protein from the host cells or from the culture medium.

31. The method of claim 24, wherein the administration comprises administering a composition comprising the fusion protein of claim 1.

* * * * *

UNITED STATES PATENT AND TRADEMARK OFFICE
CERTIFICATE OF CORRECTION

| | |
|---|---|
| PATENT NO. | : 7,939,632 B2 |
| APPLICATION NO. | : 12/000739 |
| DATED | : May 10, 2011 |
| INVENTOR(S) | : Hubert Metzner et al. |

It is certified that error appears in the above-identified patent and that said Letters Patent is hereby corrected as shown below:

Claim 1, column 83, line 5, "half-life enhancing polypeptide is, and" should read -- half-life enhancing polypeptide is albumin, and --.

Signed and Sealed this
Sixteenth Day of August, 2011

David J. Kappos
*Director of the United States Patent and Trademark Office*

UNITED STATES PATENT AND TRADEMARK OFFICE
CERTIFICATE OF CORRECTION

PATENT NO. : 7,939,632 B2
APPLICATION NO. : 12/000739
DATED : May 10, 2011
INVENTOR(S) : Hubert Metzner et al.

Page 1 of 1

It is certified that error appears in the above-identified patent and that said Letters Patent is hereby corrected as shown below:

Claim 13, column 84, line 9, "FVIIaITF" should read -- FVIIa/TF --.

Signed and Sealed this
Sixth Day of September, 2011

David J. Kappos
*Director of the United States Patent and Trademark Office*